US010271581B2

(12) United States Patent
Kehler et al.

(10) Patent No.: US 10,271,581 B2
(45) Date of Patent: Apr. 30, 2019

(54) RECOVERY TIGHT WITH PRECONFIGURED COMPRESSION ZONES AND INTEGRATED STRUCTURE PATTERNS

(71) Applicant: NIKE, Inc., Beaverton, OR (US)

(72) Inventors: Alyse Kehler, Portland, OR (US); Richa Maheshwari, Hillsboro, OR (US); Martine Mientjes, Beaverton, OR (US); Christopher J. Ranalli, Portland, OR (US); Susan L. Sokolowski, Portland, OR (US); Andrea J. Staub, Portland, OR (US); Heidi A. Vaughan, Lake Oswego, OR (US)

(73) Assignee: NIKE, Inc., Beaverton, OR (US)

( * ) Notice: Subject to any disclaimer, the term of this patent is extended or adjusted under 35 U.S.C. 154(b) by 175 days.

(21) Appl. No.: 15/151,916

(22) Filed: May 11, 2016

(65) Prior Publication Data

US 2016/0338417 A1 Nov. 24, 2016

Related U.S. Application Data

(60) Provisional application No. 62/165,475, filed on May 22, 2015.

(51) Int. Cl.
*A41B 11/00* (2006.01)
*A61F 13/08* (2006.01)

(52) U.S. Cl.
CPC ............ *A41B 11/003* (2013.01); *A61F 13/08* (2013.01); *A41B 2500/10* (2013.01)

(58) Field of Classification Search
CPC ... A41B 11/00; A41B 11/003; A41B 2500/00; A41B 2500/10; A41D 17/00;
(Continued)

(56) References Cited

U.S. PATENT DOCUMENTS

| | | | |
|---|---|---|---|
| 1,367,065 A | 2/1921 | McCrahon | |
| 1,817,053 A * | 8/1931 | Zerk | A41B 11/00 2/239 |

(Continued)

FOREIGN PATENT DOCUMENTS

| | | |
|---|---|---|
| CN | 1981653 A | 6/2007 |
| CN | 201563647 U | 9/2010 |

(Continued)

OTHER PUBLICATIONS

International Preliminary Report on Patentability dated Dec. 7, 2017 in International Patent Application No. PCT/US2016/031492, 8 pages.

(Continued)

*Primary Examiner* — Timothy K Trieu
(74) *Attorney, Agent, or Firm* — Shook, Hardy and Bacon LLP

(57) ABSTRACT

A recovery tight having preconfigured compression zones with integrated knit structures is provided herein. The compression zones may have differing compressive properties where zones having a higher compression force are located at the calf and ankle areas of the tight, zones having the next highest compression force are located over the knee and lower thigh areas of the tight, and zones having the lowest compression force are located over the upper thigh and lower torso areas of the tight when the tight is worn. The integrated knit structures modify the compressive properties of the zones in the areas where the structures are located in order to further customize the compressive properties of the recovery tight.

16 Claims, 17 Drawing Sheets

100 105 110 116 124 126 112 114 118 130 120 132

(58) Field of Classification Search
CPC .. A41D 17/02; A41D 13/0015; A41D 13/012; A41D 27/08; A61F 13/08
USPC .......................................... 2/239, 242, 241
See application file for complete search history.

(56) References Cited

U.S. PATENT DOCUMENTS 3,429,147 A 2/1969 Perrier
3,703,820 A 11/1972 Jackson
3,748,870 A 7/1973 Fregeolle
4,027,667 A * 6/1977 Swallow .................. D04B 9/52 602/63
4,086,790 A * 5/1978 Hanrahan, Jr. ........ D04B 1/265 66/178 A
4,089,064 A * 5/1978 Chandler, Jr. ....... A41B 11/003 2/404
4,156,294 A * 5/1979 Horn ...................... A63B 71/12 2/239
4,172,456 A * 10/1979 Zens ....................... A61F 13/08 2/240
4,176,665 A * 12/1979 Terpening ............... A61F 13/08 2/239
4,180,065 A * 12/1979 Bowen .................... A61F 13/08 2/239
4,213,312 A 7/1980 Cassidy, Sr. et al.
4,240,160 A 12/1980 Imboden et al.
4,422,307 A * 12/1983 Thorneburg ......... A41B 11/003 2/239
4,502,301 A * 3/1985 Swallow ................. A61F 13/08 602/62
4,513,740 A * 4/1985 Westlake .............. A61F 13/085 602/62
4,527,403 A 7/1985 Fullbright et al.
5,125,116 A * 6/1992 Gaither .................. A41B 11/00 2/239
5,367,708 A * 11/1994 Fujimoto ........... A41D 13/0015 2/22
5,581,817 A * 12/1996 Hicks ..................... A41B 11/00 2/22
5,823,013 A 10/1998 Lonati et al.
6,012,177 A * 1/2000 Cortinovis .............. A61F 13/08 2/239
6,053,852 A * 4/2000 Wilkinson ......... A41D 13/0015 2/69
6,119,491 A 9/2000 Pinelli
6,216,495 B1 * 4/2001 Couzan ................... A61F 13/08 2/239
6,341,506 B1 * 1/2002 Myers .................... A41B 11/14 66/178 R
7,159,621 B2 1/2007 Shannon
7,434,423 B1 * 10/2008 Reid, Jr. ................ A61F 13/08 66/178 A
7,856,668 B2 * 12/2010 Demarest ................. A41D 7/00 2/69
8,296,864 B2 * 10/2012 Torry ....................... A41D 1/08 2/69
8,425,324 B2 4/2013 Kemmerling et al.
8,578,512 B2 * 11/2013 Moore .................... B63C 11/04 2/2.15
9,777,413 B2 * 10/2017 Messier ................... D04B 9/52
2001/0013138 A1 * 8/2001 Myers .................... A41B 11/14 2/239
2002/0152775 A1 10/2002 Browder, Jr.
2006/0169004 A1 * 8/2006 Belluye .................. A41D 1/084 66/177
2008/0120757 A1 * 5/2008 Nakazawa ......... A41D 13/0015 2/22
2010/0130903 A1 * 5/2010 Rock ...................... A61F 13/06 602/62
2011/0257575 A1 * 10/2011 Farrow ................... A61F 13/08 602/75
2011/0302686 A1 * 12/2011 Chapuis ............. A41D 13/0015 2/69
2012/0117706 A1 * 5/2012 Tateo .................. A41D 13/065 2/24
2012/0174282 A1 * 7/2012 Newton ............ A41D 13/0015 2/69
2013/0186150 A1 7/2013 Pilawa et al.
2013/0254971 A1 10/2013 Galluzzo et al.
2014/0000005 A1 1/2014 Berns et al.
2014/0075656 A1 * 3/2014 Chang ................ A41D 13/0015 2/455
2014/0082815 A1 * 3/2014 Harber .............. A41D 13/0015 2/69
2014/0289924 A1 * 10/2014 Cleveland .............. A61F 13/08 2/2.5
2014/0366585 A1 * 12/2014 Shen ................. A41D 13/0015 66/175
2015/0025435 A1 * 1/2015 Sherman ............... A61F 5/0111 602/28
2015/0051524 A1 * 2/2015 Messier .................. A61F 13/08 601/84
2015/0224011 A1 * 8/2015 Scott ...................... A61H 7/001 601/84
2016/0150835 A1 * 6/2016 Salmini ............. A63B 71/1225 428/134
2016/0338417 A1 * 11/2016 Kehler ................. A41B 11/003
2016/0338424 A1 * 11/2016 Kehler ..................... A41D 1/08
2016/0339286 A1 * 11/2016 Kehler ............. A63B 21/00178
2018/0035727 A1 * 2/2018 Cumiskey .......... A41D 13/0015
2018/0049482 A1 * 2/2018 Erkus ....................... A41D 1/06
2018/0279694 A1 10/2018 Theno et al.

FOREIGN PATENT DOCUMENTS

CN 203072932 U 7/2013
CN 103747695 A 4/2014
EP 0964091 A2 12/1999
EP 2543267 A1 1/2013
FR 2958535 A1 10/2013
GB 803083 A 10/1958
GB 2117805 A 10/1983
JP H05125601 A 5/1993
JP H11158704 A 6/1999
WO 2009135474 A1 11/2009
WO 2012164300 A1 12/2012

OTHER PUBLICATIONS

International Preliminary Report on Patentability dated Dec. 7, 2017 in International Patent Application No. PCT/US2016/031493, 9 pages.
International Preliminary Report on Patentability dated Dec. 7, 2017 in International Patent Application No. PCT/US2016/031495, 9 pages.
"Textured Leggings" gobellygowear.com Last accessed Feb. 25, 2015 http://shop.gobellygowear.com/TexturedLeggingsTEXTURE.htm.
"Maruska Tights" anthropologie.com Last accessed Feb. 25, 2015 http://us.anthropologie.com/anthro/product/26072843.jsp#/.
"1×1 rib texture merino wool knit tights double gusset yellow" Last accessed Feb. 25, 2015 https://www.robaversand.com/en/11ribtexturemerinowoolknittightsdoublegussetyellow.html.
International Search Report with Written Opinion dated Jul. 20, 2016 in International Application No. PCT/US2016/031493, 13 pages.
International Search Report and Written Opinion dated Jul. 20, 2016 in International Patent Application No. PCT/US2016/031493, 13 pages.
International Search Report and Written Opinion dated Jul. 20, 2016 in International Patent Application No. PCT/US2016/031495, 13 pages.
Non-Final Office Action dated Aug. 3, 2018 in U.S. Appl. No. 15/151,928, 13 pages.
Final Office Action dated Sep. 20, 2018 in U.S. Appl. No. 15/151,924, 8 pages.
Communication pursuant to Article 94(3) dated Dec. 6, 2018 in European Patent Application No. 16725007.5, 5 pages.

(56) References Cited

OTHER PUBLICATIONS

Notice of Allowance dated Dec. 12, 2018 in U.S. Appl. No. 15/151,924, 6 pages.
Final Office Action dated Dec. 21, 2018 in U.S. Appl. No. 15/151,928, 18 pages.

* cited by examiner

RECOVERY TIGHT WITH PRECONFIGURED COMPRESSION ZONES AND INTEGRATED STRUCTURE PATTERNS

CROSS-REFERENCE TO RELATED APPLICATIONS

This application having U.S. patent application Ser. No. 15/151,916, entitled "Recovery Tight with Preconfigured Compression Zones and Integrated Structure Patterns," and filed May 11, 2016, is a Non-Provisional Application claiming priority to U.S. Prov. App. No. 62/165,475, entitled "Recovery Tight with Preconfigured Compression Zones and Integrated Structure Patterns," and filed May 22, 2015. The entirety of the aforementioned application is incorporated by reference herein.

This application having U.S. patent application Ser. No. 15/151,916, entitled "Recovery Tight with Preconfigured Compression Zones and Integrated Structure Patterns," and filed May 11, 2016 is related by subject matter to concurrently filed U.S. application Ser. No. 15/151,928, entitled "Running Tight with Preconfigured Compression Zones and Integrated Structure Patterns," and filed May 11, 2016, and U.S. application Ser. No. 15/151,924, entitled "Training Tight with Preconfigured Compression Zones and Integrated Structure Patterns," and filed May 11, 2016. The entireties of the aforementioned applications are incorporated by reference herein.

FIELD

The present disclosure relates to a warp knit recovery tight having preconfigured compression zones.

BACKGROUND

Recovery from athletic training is an essential part of the training process. This can involve such things as building in rest days, massages, ice baths, hydration, taking non-steroidal anti-inflammatories, and the like. Some of these measures, such as massages, ice baths, and non-steroidal therapy are used to help reduce the amount of inflammation, swelling, edema, and lactic acid build-up triggered by strenuous training. As a practical matter, the edema engendered by this type of training often occurs in the ankle and calf area of the athlete due to the effects of gravity. Traditional training apparel often fails to address these consequences of training as its focus tends to be more on comfort, breathability, and the like.

BRIEF DESCRIPTION OF THE DRAWINGS

Examples of the present invention are described in detail below with reference to the attached drawing figures, wherein.

DETAILED DESCRIPTION

Figure 2:
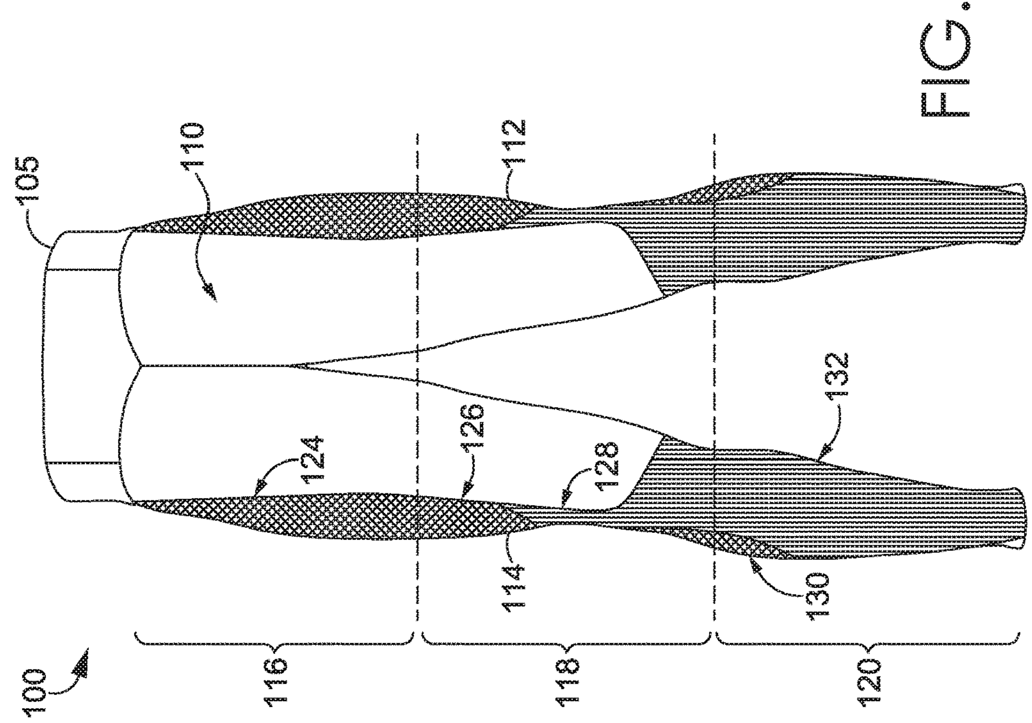
FIG. 2 illustrates a back view of the exemplary recovery tight with preconfigured compression zones and integrated structure patterns of FIG. 1 in accordance with an aspect herein.

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

At a high level, aspects herein are directed toward a warp knit recovery tight having preconfigured compression zones with different compressive properties. The different compressive properties of the zones are achieved by varying the modulus of elasticity of the yarns used to form the tights, and/or by varying the modulus of elasticity of the fabric through yarn placement, and/or by using integrated knit structure patterns that modify the compressive properties of the zones in areas where the patterns are located. The recovery tights are configured such that a relatively high amount of compression is distributed over the ankle and calf area of the wearer when the recovery tight is worn, a medium amount of compression is distributed over the knee and lower thigh area of the wearer, and a low amount of compression is distributed over the upper thigh and lower torso area of the wearer when the recovery tight is worn. The amount of compression applied to a localized area on the wearer may be fine-tuned through use of the integrated knit structure patterns. These patterns generally comprise a plurality of offset areas created by shortening the length of the stitch used in this area. By shortening the stitch length, the modulus in the offset area is increased. The result of the configuration described is that edema may be minimized in the calf and ankle areas of the wearer. Moreover, a beneficial level of compression may be achieved over the large muscle groups in the thigh area helping to minimize any possible swelling and/or production of edema in this area. For instance, by configuring the tight such that compression is greatest at the calf and ankle areas of the tight and gradually decreases towards the lower torso portion of the tight, any edema that has developed in the lower part of the wearer's extremities is "squeezed" upwards toward the wearer's trunk where resorption is enhanced.

Aspects herein may further relate to a method of manufacturing a recovery tight. The method may comprise, for example, preparing a warp knitting machine (single or double bar Jacquard) to utilize different elastic yarns having different moduli of elasticity in the warp where the yarns having different moduli of elasticity correspond to the different zones discussed above. Continuing, the method may further comprise programming the warp knitting machine based on a preconfigured placement pattern of the integrated knit structures. Next, a fabric is warp knitted and one or more pattern pieces are cut from the fabric. The pattern pieces are then affixed together to form the recovery tight. Additional steps may comprise dyeing and finishing the tight. In aspects, the dyeing and finishing may occur prior to cutting and affixing the pattern pieces together. Tights formed through this type of warp knitting process exhibit four-way stretch allowing them to closely conform to the wearer's body when worn. Moreover, materials used to form the tights are selected to provide breathability, moisture-management properties, and opacity to the tight.

Accordingly, aspects herein are directed to a recovery tight comprising a plurality of compression zones, where each of the plurality of compression zones has a compression force within a predefined range, and where one or more of the plurality of compression zones has an integrated structure pattern that modifies the compression force of the respective compression zone.

In another aspect, aspects herein are directed to a recovery tight comprising a first compression zone having a first compression force within a predefined range, where the first compression zone is located at an upper portion of the recovery tight and a second compression zone having a second compression force within a predefined range, where the second compression zone located adjacent to and below the first compression zone. The recovery tight further comprises a third compression zone having a third compression force within a predefined range, where the third compression zone is located adjacent to and below the second compression zone. In aspects, one or more of the first, second, and third compression zones comprises one or more integrated structure patterns that modify the compression force of the respective compression zone.

In yet another aspect, a method of manufacturing a recovery tight is provided. The method comprises preparing a fabric, where preparing the fabric comprises knitting a first compression zone having a first compression force and a first integrated knit structure pattern; knitting a second compression zone having a second compression force and a second integrated knit structure pattern; and knitting a third compression zone having a third compression force and a third integrated knit structure pattern. The method further comprises cutting one or more pattern pieces from the fabric and affixing the one or more pattern pieces together at one or more seams to form the recovery tight.

As used throughout this disclosure, the term "elastic yarn" is meant to encompass both natural and synthetic yarns, fibers, and/or filaments that have the ability to be stretched and to quickly return to their original form. Exemplary elastic yarns, fibers, and/or filaments include Lycra, thermoplastic polyurethane (TPU), elastane, rubber, latex, spandex, combinations thereof, and the like. The elastic yarns may be used by themselves to form the tights, or they may be combined with other types of yarns or fibers such as cotton, nylon, rayon, wool, polyester, or other fiber types to form the tights. In one exemplary aspect, these non-elastic yarns may comprise 50 denier polyester yarns. Further, as used throughout this disclosure, the term "modulus of elasticity" may be defined as a measure of an object's resistance to being deformed elastically when a force is applied to it. Modulus values, as described herein, are measured at 30% stretch across the width of the tight by ASTM D4964 and are expressed in pound-force (lbf). The term "compression force" as used herein is a measure of the pushing or pressing force that is directed toward the center of an object. The compression force is measured by a Salzmann Device and is expressed as a surface pressure value in mmHg.

Further, as used throughout this disclosure, the term "tight" may be defined as an article of clothing that closely conforms to the body contours of a wearer. This may be achieved by, for instance, incorporating elastic yarns into the tight as explained above. The term tight may refer to a full legging, a capri-style tight, a half-tight, a three-quarter tight, or a pair of shorts. In exemplary aspects, the tight may comprise a base layer worn under other layers of clothing. However, it is also contemplated herein that the tight may be worn by itself (i.e., not covered by other layers).

Figure 1:
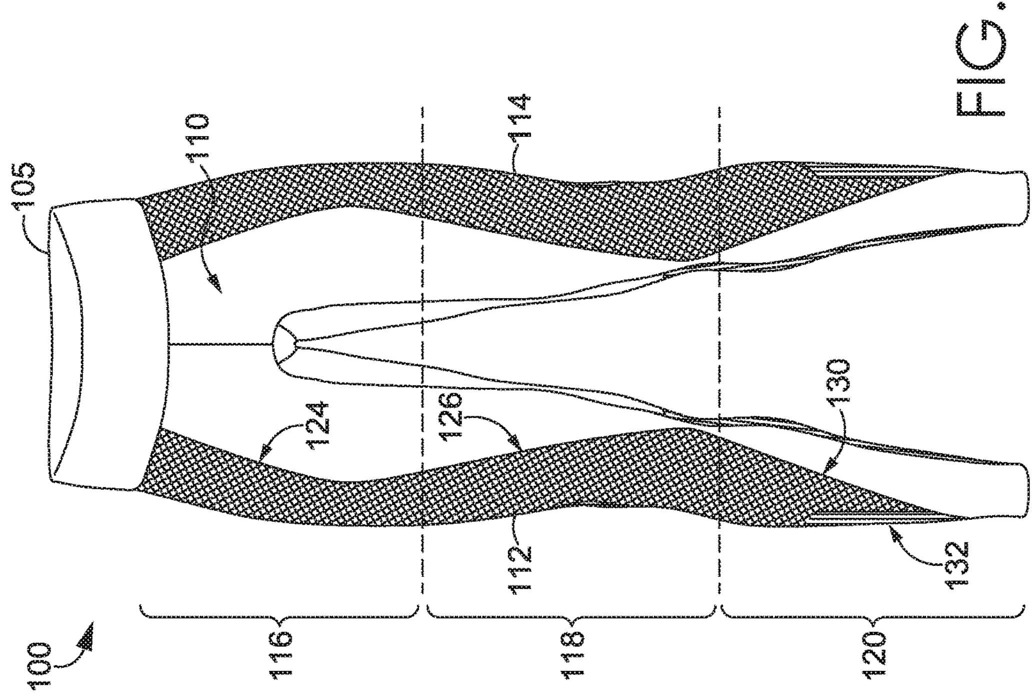
FIG. 1 illustrates a front view of an exemplary recovery tight with preconfigured compression zones and integrated structure patterns in accordance with an aspect herein.

Turning now to FIG. 1, a front view of an exemplary recovery tight 100 having compression zones and integrated knit structure patterns is depicted in accordance with an aspect herein. In exemplary aspects, the recovery tight 100 may be formed from a textile or panel knitted using a single bar Jacquard warp knitting process. The recovery tight 100 may comprise an optional waistband 105 affixed to a lower torso portion 110, where the lower torso portion 110 is adapted to cover a lower torso of a wearer when the tight 100 is worn. The recovery tight 100 may further comprise a first leg portion 112 and a second leg portion 114 adapted to cover the legs of the wearer when the tight 100 is worn. Although shown as a full legging, it is contemplated that the recovery tight 100 may be in the form of a capri-type style, a half-tight, a three-quarter tight, or a short.

In exemplary aspects, the tight 100 may be divided into three compression zones, 116, 118, and 120 wherein at least two of the compression zones may exhibit different compressive properties. In exemplary aspects, the three compression zones 116, 118, and 120 may be in a generally horizontal orientation on the tight 100 when worn due to the single bar Jacquard warp knitting process. It is contemplated herein that the tight 100 may include more or less than the three compression zones. The use of the term "compression zone" is meant to convey the functional characteristics of the tight 100 and is not meant to imply a specific shape, size, color, pattern, or orientation. For example, the recovery tight 100 may visually appear to have a generally uniform surface with no clear demarcation between the different zones.

The different compressive properties of the compression zones 116, 118, and 120 may be created by, for example, using elastic yarns of differing diameter or differing denier in the warp. Elastic yarns having a higher denier or larger diameter will generally have a higher modulus of elasticity as compared to yarns having a smaller denier or a smaller diameter. Elastic yarns contemplated herein may have deniers ranging from, for example, 20 denier up to 160 denier. In an exemplary aspect, the compressive property of a particular zone may be created by using elastic yarns all having the same denier. For instance, 40 denier yarns may be used to knit a compression zone having a generally low modulus of elasticity, while 70 denier yarns may be used to knit a compression zone having a generally medium modulus of elasticity. In another exemplary aspect, the compressive property of a zone may be created by combining elastic yarns having different deniers. As an example, 40 denier yarns may be used with 70 denier yarns (for a combined denier of 110) to knit a compression zone having a generally high modulus of elasticity. Other combinations of deniers are contemplated herein. For instance, for compression zones having a generally medium to high compression force or modulus of elasticity, other combinations may comprise 20 denier yarns with 60 denier yarns for a combined denier of 80, 30 denier yarns with 50 denier yarns for a combined denier of 80, 40 denier yarns with 40 denier yarns for a combined denier of 80, and the like. Any and all such aspects, and any variation thereof, are contemplated as being within the scope herein.

In exemplary aspects, the first zone 116 generally extends from an upper margin of the tight 100 to approximately midway along the thigh area of the leg portions 112 and 114 (e.g., approximately one-third the length of the tights 100). In exemplary aspects, the first zone 116 may be constructed to have an overall compression force in the range of approximately 4.0 to 13.0 mmHg, 4.2 to 12.75 mmHg, or 4.5 to 12.0 mmHg. By distributing a relatively low amount of compression over the lower torso and upper thigh areas of the wearer, a high degree of mobility is maintained in this area while a beneficial amount of compression is provided.

In exemplary aspects, the first zone 116 may have a first integrated structure pattern comprising a series of shapes 124 in the form of diamonds. As mentioned, the compression force and/or modulus associated with a particular compression zone, such as the first zone 116, may be modified by use of knit structure patterns that are integrally formed from the same yarns used to knit the compression zones. The knit structure pattern generally comprises a pattern of offset, depressed areas in the fabric (areas of the fabric that extend inwardly away from the outer-facing surface plane of the tight 100). In exemplary aspects, these offset, depressed areas surround and define different structures or shapes. For example, the structure may comprise a series of lines created when the offset, depressed areas define a plurality of lines. In another example, a shape pattern may be created when the offset, depressed areas define a plurality of geometric shapes such as diamonds, squares, chevrons, and the like. In some exemplary aspects, the offset, depressed areas themselves may form shapes such as circles, diamonds, square, and the like, and the remaining portions of the tight surrounds these offset shapes. Any and all such aspects, and any variation thereof, are contemplated as being within the scope herein.

The integrated knit structure patterns are created by, for instance, changing the length of the knit stitches. For example, a shorter stitch may be used to knit the offset, depressed areas of the pattern. Because a shorter stitch is used, these depressed areas typically exhibit less stretch due to less yarn and/or shorter floats in the stitch. And because these areas exhibit less stretch, the modulus of elasticity and/or compression force associated with these offset areas is increased. Thus, in general, the modulus of elasticity or compression force associated with the knit structure patterns is greater than the modulus of elasticity and/or compression force in the areas of the tight 100 where the knit structure patterns are not located.

Figure 4:
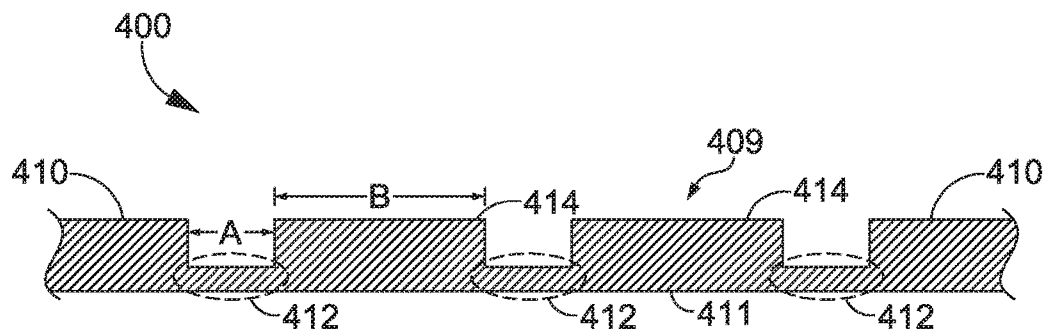
FIG. 4 illustrates a cross-section of an exemplary recovery tight taken at the location of an integrated structure pattern in accordance with an aspect herein.

A depiction of a cross-section of a fabric having an integrated knit structure pattern, referenced generally by the numeral 400, is illustrated in FIG. 4 in accordance with an aspect herein. In exemplary aspects, the fabric having the integrated knit structure pattern 400 may be incorporated into a tight, such as the recovery tight 100. As such, the reference numeral 410 indicates the portion of the tight on either side of or surrounding the integrated knit structure pattern 400. The offset, depressed areas created by using the shorter length stitch are indicated by the reference numeral 412. As shown, the areas 412 are offset from or extend inwardly from the outer-facing surface 409 of the tight and have an exemplary width “A.” As such, the outer-facing surface 409 of the tight is non-planar while an inner-facing surface 411 of the tight is planar as shown in FIG. 4. In exemplary aspects, the width A of the offset areas 412 may range from 0.5 mm up to 10 mm. In exemplary aspects, the offset areas 412 may delineate, space apart, and/or define a set of structures 414 having a width “B.” The width B of the structures 414 may range from 0.5 mm up to 10 mm. The structures 414 are knit with generally the same stitch length as portions of the tight that do not have integrated structure patterns. As such, the “height” of the structures 414 generally align with the outer-facing surface plane of the tights. To put it another way, the structures 414 generally do not extend past the outer-facing surface plane of the tights. Depending on the pattern of the offset areas 412, the structures 414 may comprise lines or shapes such as those described with respect to FIGS. 5A-5S below. In another exemplary aspect, the offset areas 412 may themselves have a defined shape such as a circle, square, diamond, and the like. In this aspect, the non-offset areas of the tight surround and help to define these offset shapes. Any and all such aspects, and any variation thereof, are contemplated as being within the scope herein.

As described, the modulus of elasticity or compression force associated with a particular compression zone may be increased by use of integrated knit structure patterns such as the integrated knit structure pattern 400. The amount of increase may be tailored or customized by increasing and/or decreasing the percentage, amount, and/or surface area of the offset, depressed areas, such as the offset areas 412 of FIG. 4, in the particular knit structure pattern. As an example, by increasing the amount, percentage, or surface area of offset, depressed areas in a particular knit structure pattern, the compression force and/or modulus of elasticity in the knit structure pattern may be further increased. To describe it in a different way, the compression force and/or modulus of elasticity in a particular knit structure pattern may be further increased by increasing the spacing between adjacent structures in the pattern since the spacing corresponds to the offset areas (e.g., the spacing corresponds to the width A in FIG. 4). Conversely, by decreasing the amount, percentage, or surface area of offset, depressed areas in a particular knit structure pattern, the compression force and/or modulus associated with the knit structure pattern may be decreased relative to those areas of the pattern that have a higher percentage or surface area of offset areas. To put it another way, the compression force and/or modulus of elasticity in a particular knit structure pattern may be relatively decreased by decreasing the spacing between adjacent structures in the pattern.

Continuing, the orientation and/or direction of the offset areas within a particular knit structure pattern in relation to the tight as a whole may be used to modify the direction of the compression force and/or modulus of elasticity associated with the pattern. As an example, when the offset areas are in the form of lines, by orienting the offset lines in a generally vertical direction on the tight, the modulus associated with the pattern may be modified in a first vertical direction but be generally unmodified in a horizontal direction. However, by orienting the offset lines in the pattern in a generally horizontal direction, the modulus associated with the pattern may be modified in a second horizontal direction but be unmodified in the vertical direction. Any and all such aspects, and any variation thereof, are contemplated as being within aspects herein.

Figure 5A:
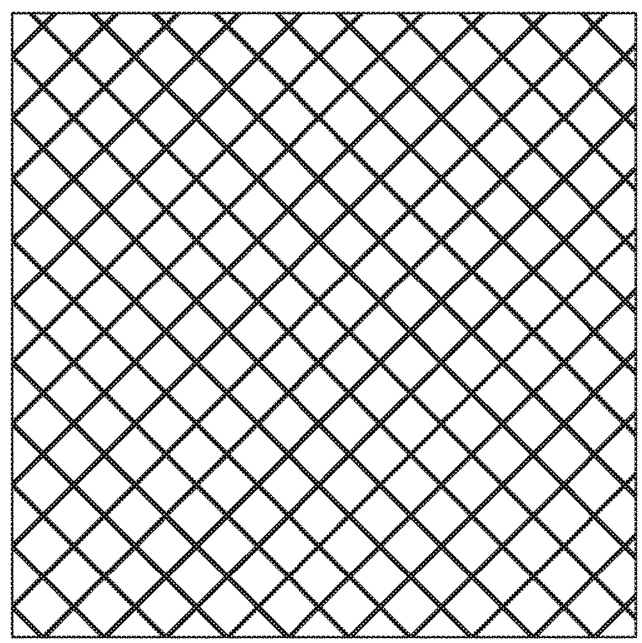
FIGS. 5A-5S illustrate exemplary configurations and exemplary spacings for the integrated structure patterns in accordance with aspects herein.
Figure 5B:
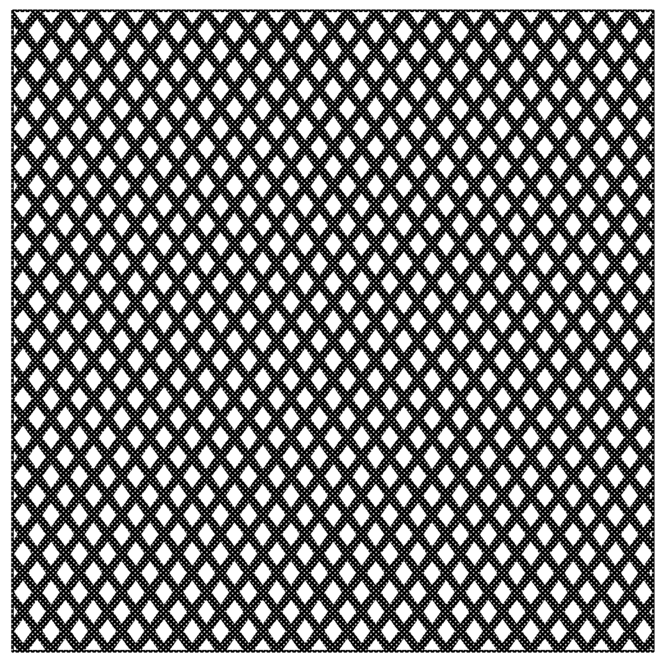
Figure 5C:
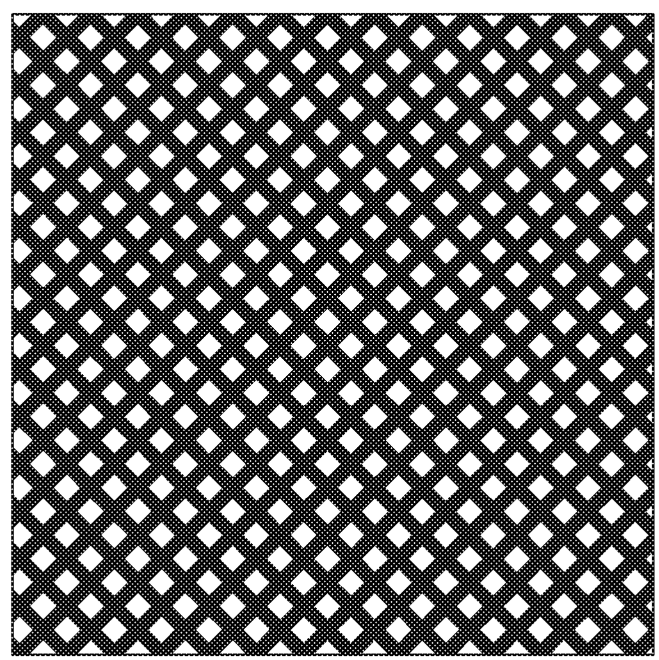
Figure 5D:
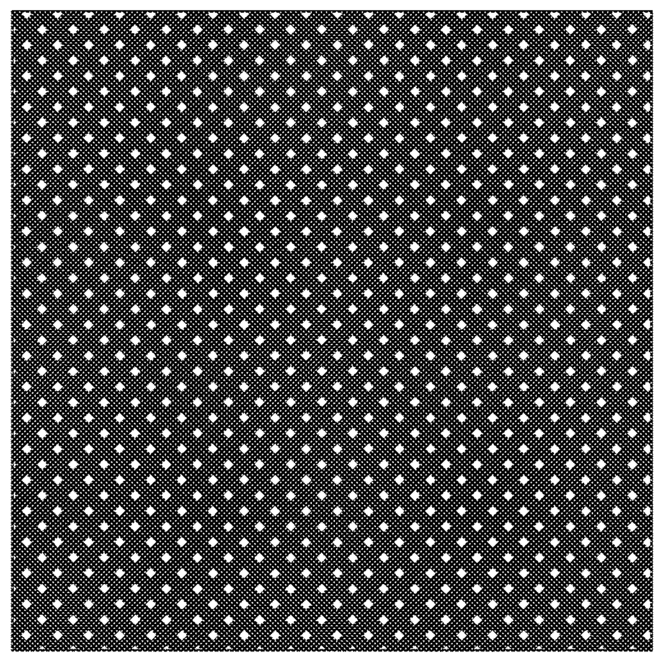
Figure 5E:
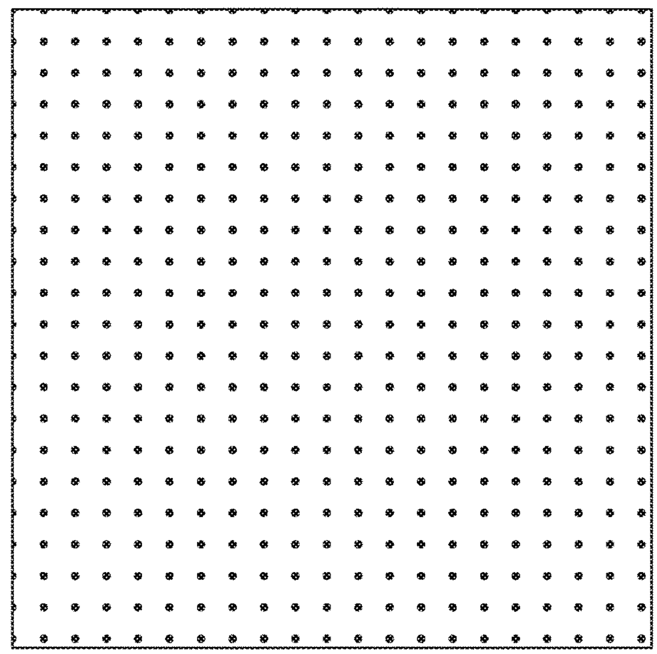
Figure 5F:
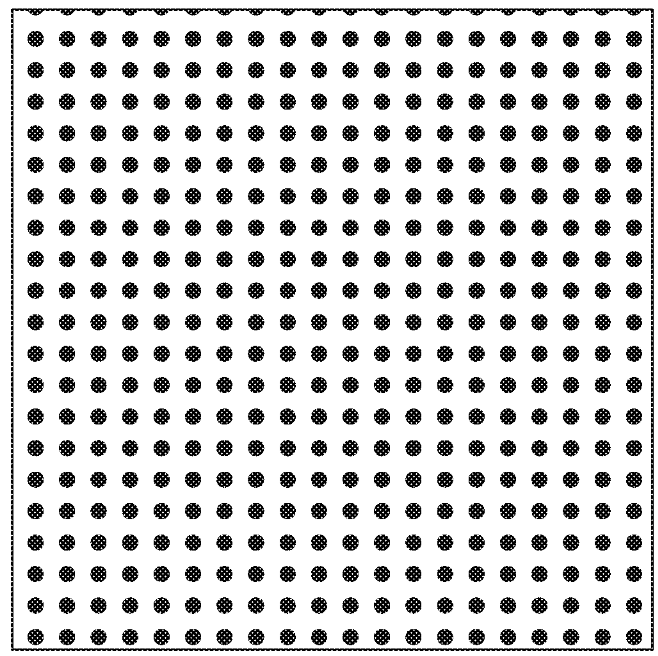
Figure 5G:
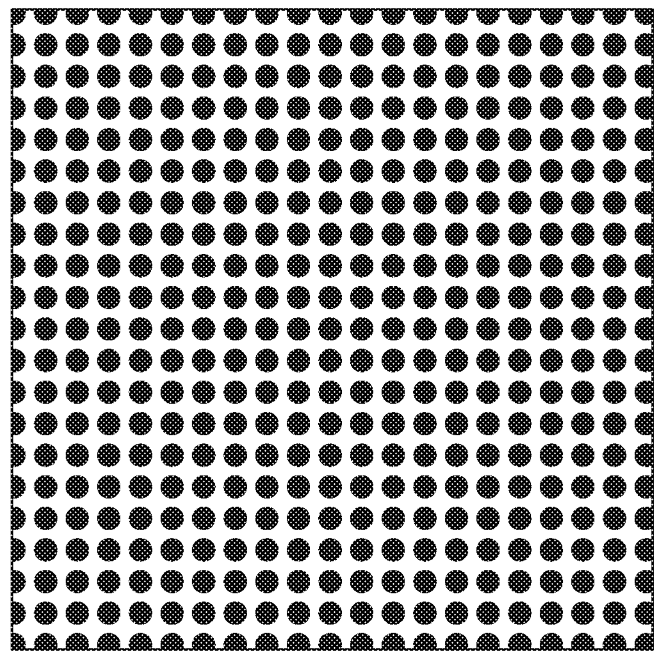
Figure 5H:
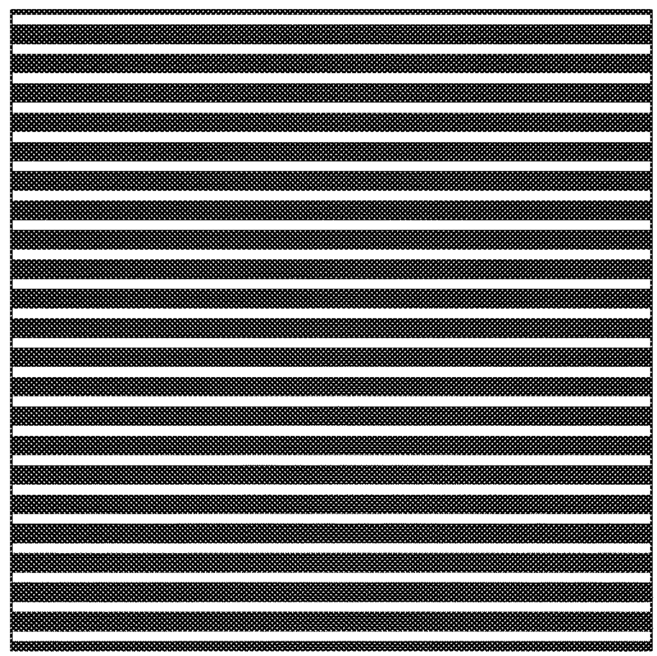
Figure 5I:
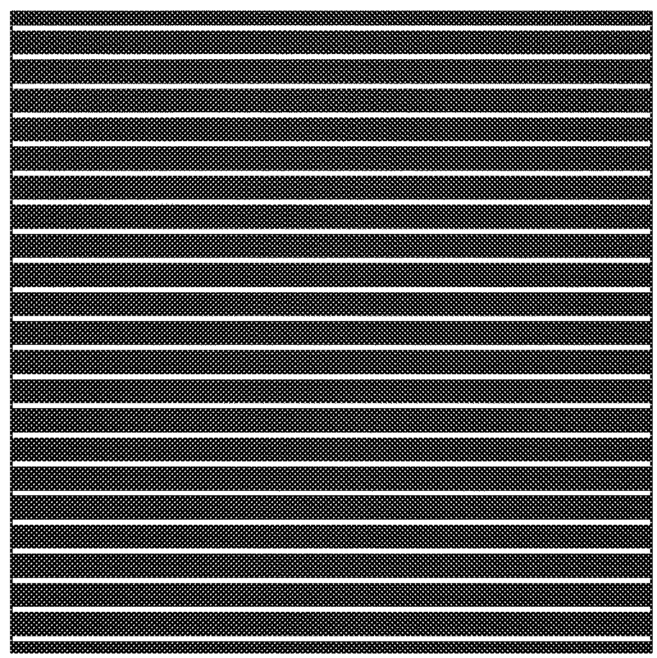
Figure 5J:
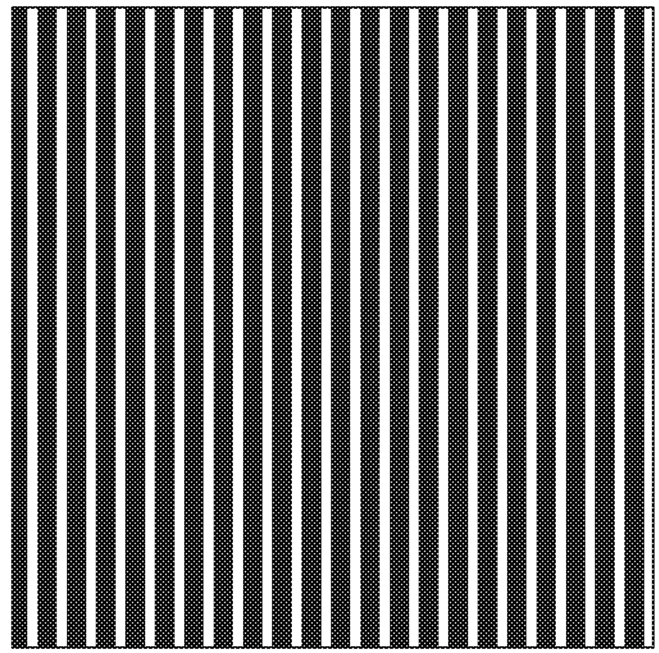
Figure 5K:
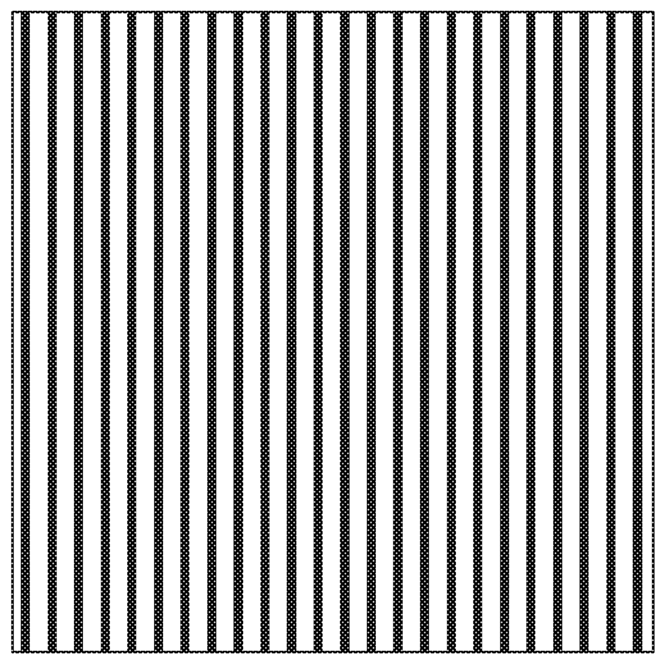
Figure 5L:
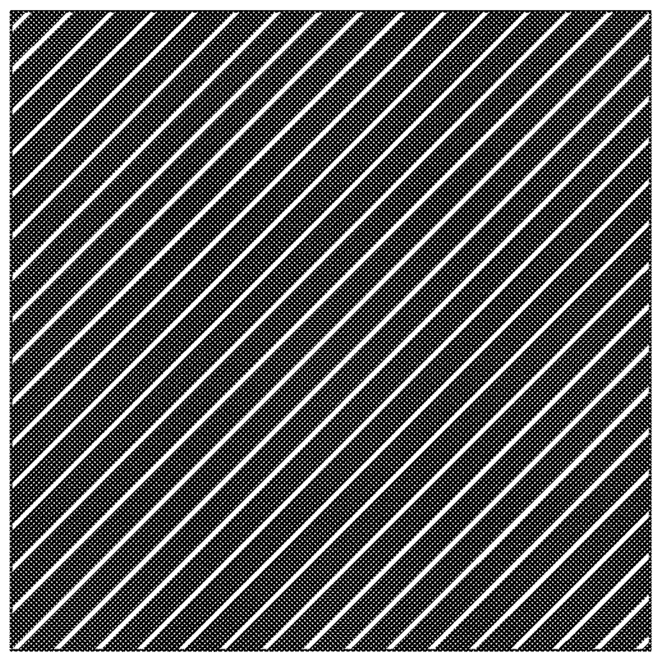
Figure 5M:
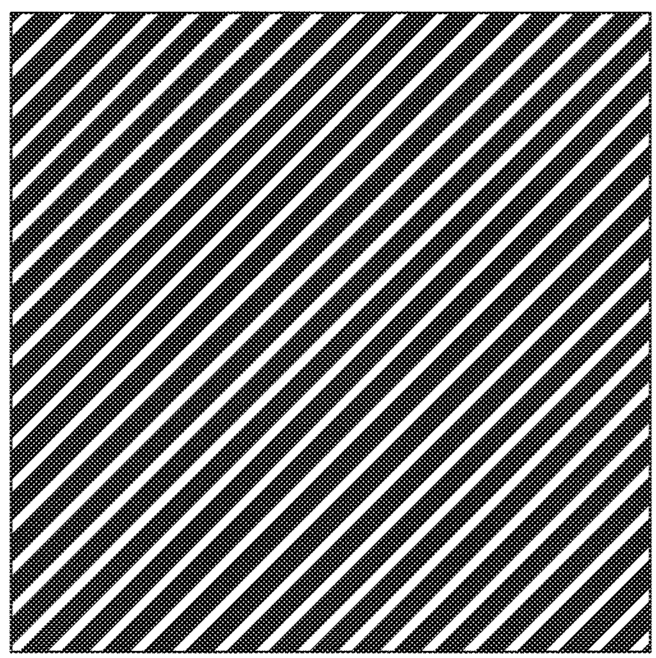
Figures 5N, 5O:
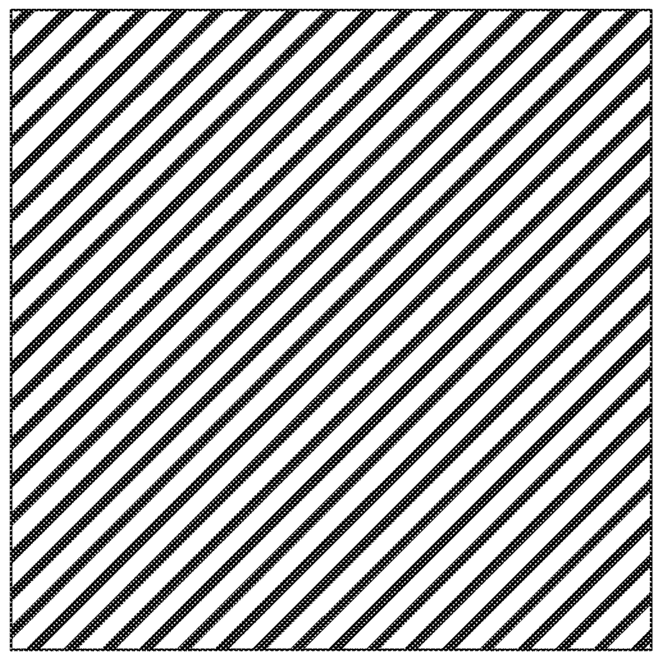
Figure 5P:
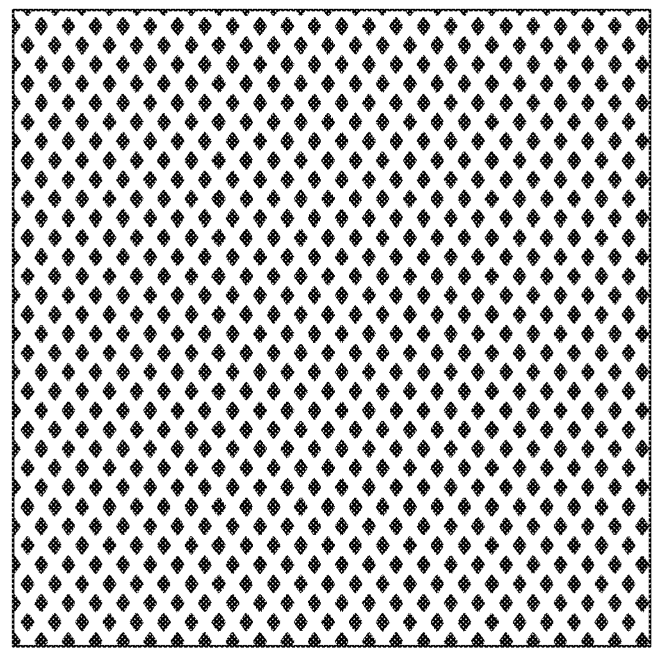
Figure 5Q:
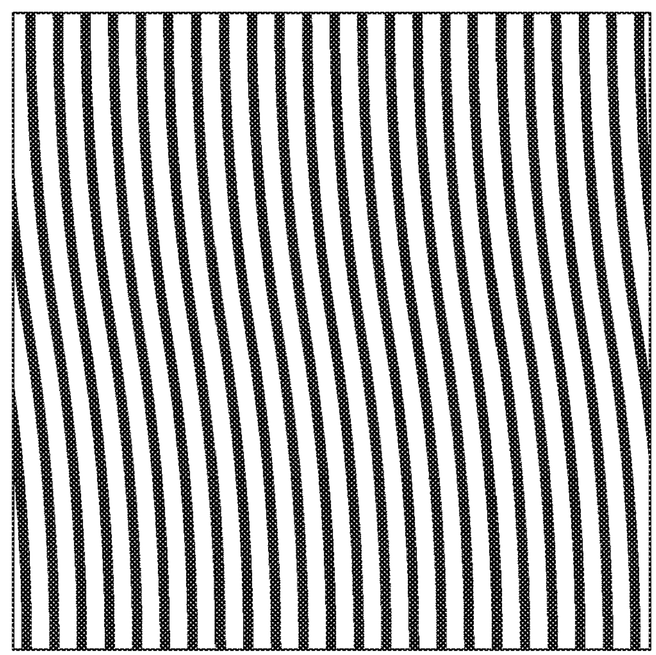
Figure 5R:
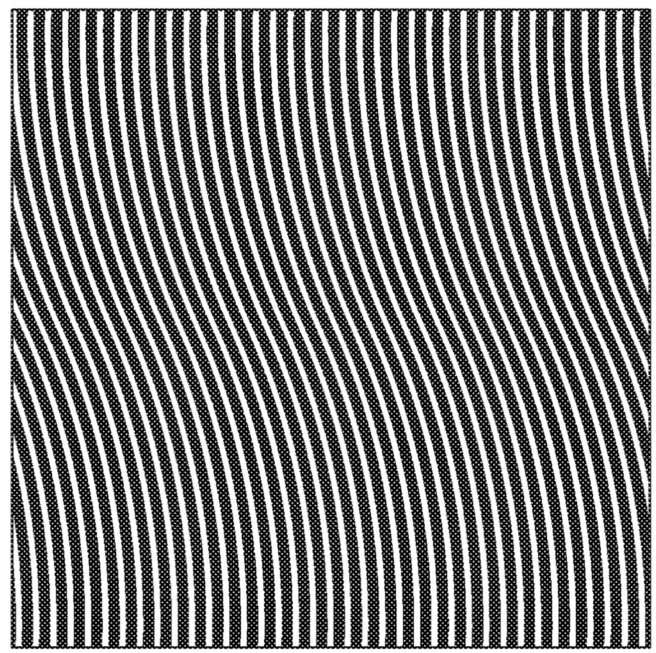
Figure 5S:
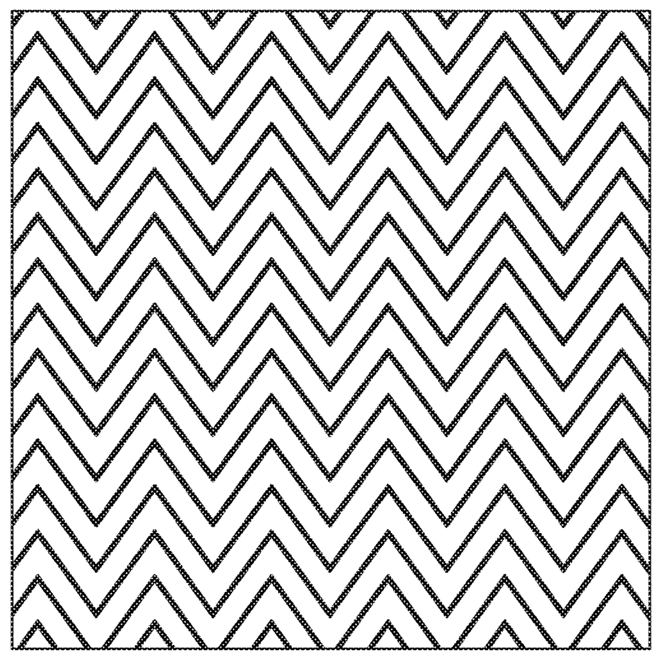

FIGS. 5A-5S illustrate a number of examples of integrated structure patterns as contemplated herein. The offset areas are shown in black and the structures defined by the offset areas are shown in white. For instance, FIGS. 5A-5D depict a series of diamond structures, where the spacing (e.g., the offset areas) between the diamonds gradually increases from FIG. 5A to FIG. 5D with a resultant decrease in size of the diamonds from FIG. 5A to FIG. 5D. Thus, the modulus and/or compression force associated with this pattern would increase from FIG. 5A to FIG. 5D.

FIGS. 5E-5G depict examples where the offset areas are in the form of circles and the remaining portion of the tight surrounds the circles. The size of the circles gradually increases from FIG. 5E to FIG. 5G, which would cause a corresponding increase in the modulus and/or compression force from FIG. 5E to FIG. 5G. Although circles are shown, it is contemplated herein that the offset areas may take other forms such as square, diamonds, triangles, and the like. FIGS. 5H and 5I depict a series of horizontal line structures, where the offset spacing between the lines increases from FIG. 5H to FIG. 5I with a resultant decrease in the width of the lines from FIG. 5H to FIG. 5I. Because the offset spacing in these patterns is oriented along a horizontal axis, the modulus and/or compression force would be increased along this axis.

Continuing, FIGS. 5J and 5K depict a series of vertical line structures, where the spacing between the lines decreases from FIG. 5J to FIG. 5K with a resultant increase in the width of the lines between these two figures. FIGS. 5L-5N depict a series of diagonal line structures, where the spacing between the lines decreases from FIG. 5L to FIG. 5N with a resultant increase in the width of the lines from FIG. 5L to FIG. 5N. FIG. 5O depicts a series of diagonal line structures oriented in different directions, and FIG. 5P depicts a configuration where the offset areas form diamond shapes. FIGS. 5Q-5R depict a set of curvilinear line structures separated by offset areas, where the spacing increases from FIG. 5Q to FIG. 5R with a resultant decrease in the size of the lines from FIG. 5Q to FIG. 5R. FIG. 5S depicts a series of zig-zag line structures separated by zig-zag offset spaces. Although not shown, the spacing between the zig-zag line structures may be increased or decreased with a resultant decrease or increase of the width of the zig-zag lines respectively.

As seen, the integrated knit structure patterns may take a variety of forms in order to achieve different functional purposes as outlined above. For example, by increasing the spacing between the structures (i.e., by increasing the percentage or surface area of the offset areas), a higher modulus and/or compression is achieved in the area of the tight where the pattern is located, and by decreasing the spacing between the structures (i.e., by decreasing the percentage or surface area of the offset areas), the modulus and/or compression force is reduced relative to areas of the pattern having increased spacing. Moreover, by orienting the pattern in certain directions, the modulus of elasticity may be altered along a long axis of the pattern. Using FIG. 5L as an example, by orienting the lines and offset areas along a diagonal axis, the modulus along that diagonal axis may also be increased. Although shown as diamonds, it is contemplated herein that any of the other configurations described above may be used. Any and all such aspects, and any variation thereof, are contemplated as being within the scope herein.

Returning now to FIG. 1, the shapes 124 are defined by and separated from each other by offset, depressed areas having a shorter stitch and higher modulus (described above). Although shown as diamonds, it is contemplated herein that any of the other configurations described above may be used. Any and all such aspects, and any variation thereof, are contemplated as being within the scope herein.

In exemplary aspects, the shapes 124 may be located near the lateral margins of the recovery tight 100 and may extend around to the back side of the tight 100 as will be shown in FIG. 2. As described earlier, the use of the shapes 124 may increase the modulus of elasticity and/or compression force in the underlying area of the tight 100 in which the shapes 124 are located as compared to areas of the tight 100 that do not have an integrated structure pattern. In exemplary aspects, the modulus of elasticity and/or compression force may be increased in this area by, for example, 2%, 5%, 10%, 20%, 30%, 40%, up to 50%, or any value in between.

The spacing between the shapes 124 may be adjusted along a gradient to gradually modify the modulus along the gradient. With reference to FIG. 1, the shapes 124 may be spaced closer together at the upper or superior portion of the first zone 116 and gradually become more widely spaced towards the lower or inferior portion of the first zone 116. This variation in spacing is shown in greater detail in FIG. 3. The spacing gradient between the shapes 124 may cause the modulus of elasticity and/or compression force to be further increased along the gradient by, for example, 1%, 2%, 5%, 7%, 10% up to 15% or any value in between with the larger increases being associated with the greater spacing. By locating the shapes 124 along the lateral margins of the tights 100, a greater compression force may be applied over the wearer's iliotibial (IT) band when the recovery tight 100 is worn potentially helping to facilitate recovery of this often-troubling area. Further, by spacing the shapes 124 closer together at the upper portion of the first zone 116 and by spacing the shapes 124 further apart towards the lower portion of the first zone 116, compression along the IT band is gradually increased as the distance from the wearer's core increases. The location and spacing associated with the shapes 124 are exemplary only, and it is contemplated that other locations and other spacing gradients may be utilized in association with the tight 100. Moreover, it is contemplated herein that the first zone 116 may not comprise an integrated structure pattern. Any and all aspects, and any variation thereof, are contemplated as being within the scope herein.

Continuing, the second zone 118 generally extends from the lower margin of the first zone 116 to an area slightly below the knee area of the tight 100. In exemplary aspects, the second zone 118 may be constructed to have an overall compression force that is approximately 30% greater than the compression force associated with the first zone 116. In exemplary aspects, the compression force may be in the range of 7 to 25 mmHg, 8 to 23 mmHg, or 9 to 20 mmHg.

In exemplary aspects, the second zone 118 may have an integrated structure pattern in the form of a set of shapes 126 and a set of parallel lines 128. The lines 128 may be generally positioned on the back-facing or posterior side of the tight 100 and will be described with respect to FIG. 2. The shapes 126 may comprise an extension of the shapes 124 associated with the first zone 116. The shapes 126 may be generally positioned such that they gradually extend from the lateral margin of the tight 100 to overlie the front-facing or anterior surface of the tight 100 moving from the upper portion of the zone 118 to the lower portion of the zone 118. The shapes 126 may extend towards the medial margin of the tight 100 at the lower portion of the zone 118. In exemplary aspects, spacing between the shapes 126 may be along a gradient with increased spacing between the shapes 126 located closer to the lower or inferior portion of the second zone 118. The location and spacing associated with the shapes 126 are exemplary only, and it is contemplated that other locations and other spacing gradients may be utilized in association with the tight 100. Moreover, it is contemplated herein that the second zone 118 may not comprise an integrated knit structure pattern. Any and all aspects, and any variation thereof, are contemplated as being within the scope herein.

By configuring the second zone 118 to have a compression force and/or modulus of elasticity that is greater than the compression force of the first zone 116, any edema that is present in the lower part of the extremities is assisted in its movement towards the trunk area of the wearer where its resorption may be enhanced by the body's lymphatic system. This movement is further enhanced by using the shapes 126 to increase the compression force of the tights 100 over the large muscle groups of the thigh.

The third zone 120 generally extends from the lower margin of the second zone 118 to the lower or bottom margin of the tight 100. In exemplary aspects, the third zone 120 may be constructed to have an overall compression force that is approximately 20% to 40% greater than the compression force of the second zone 118. In exemplary aspects, the compression force may be between 10 to 30 mmHg, 12 to 28 mmHg, or 15 to 25 mmHg. By providing a high compression force and/or modulus of elasticity in this area of the tight 100, the formation of edema may be minimized in the ankle and calf area of the wearer and any edema that has developed may be squeezed upward towards the lower torso of the wearer where resorption is enhanced.

In exemplary aspects, the third zone 120 may have an integrated structure pattern in the form of a set of shapes 130 and a set of parallel lines 132. The lines 132 are best shown in FIG. 2 and will be described below. The shapes 130 may comprise an extension of the shapes 126 associated with the second zone 118. As such, the shapes may be generally positioned over the front or anterior portion of shin area of the tight 100 at the upper portion of the third zone 120 and gradually taper towards the lateral margin of the tight 100 at the lower portion of the third zone 120. The spacing gradient between the shapes 130 in this area is generally the same as that between the shapes 126 at the lower margin of the second zone 118. Use of the shapes 130 in this area may provide beneficial compression over the muscles along the shin. The location and spacing associated with the shapes 130 are exemplary only, and it is contemplated that other locations and other spacing gradients may be utilized in association with the tight 100. Moreover, it is contemplated herein that the third zone 120 may not comprise an integrated knit structure pattern. Any and all aspects, and any variation thereof, are contemplated as being within the scope herein.

With respect to FIG. 2, FIG. 2 illustrates a back view of the exemplary recovery tight 100 in accordance with aspects herein. The back view of the tight 100 comprises the same zones 116, 118, and 120 as were described in relation to FIG. 1. As such, location of the zones 116, 118, and 120 and the compression force values discussed in relation to FIG. 1 with respect to the zones 116, 118, and 120 are equally applicable here. However, the location of the structures on the back or posterior portion of the tight 100 may differ from the location of the structures on the front portion of the tight 100.

In exemplary aspects, the first zone 116 on the back of the tight 100 may comprise the shapes 124 as they extend around the lateral margin of the tight 100. As such, the first zone 116 may comprise a vertical span of the shapes 124 along the lateral margin of the tights 100. Like the shapes 124 located on the front-facing or anterior side of the tight 100, spacing between the shapes 124 may gradually increase from the upper portion to the lower portion of the first zone 116. The location and spacing associated with the shapes 124 on the back portion of the tight 100 are exemplary only, and it is contemplated that other locations and other spacing gradients may be utilized in association with the tight 100.

The upper portion of the second zone 118 on the back side of the tight 100 may comprise an extension of the shapes 126 located on the front-facing side of the tight 100. As such, the shapes 126 may generally occupy an area towards the lateral margin of the tight 100. The location of the shapes 126 may generally correspond to the lower end of the wearer's IT band when the tight 100 is worn.

The lines 128 mentioned with respect to FIG. 1 generally begin at the lateral margin of the tight 100 and gradually extend posteriorly over the entirety of the second zone 118 towards the lower portion of the zone 118 such that the lines 128 generally overlay the upper calf area of the wearer when the tight 100 is worn. The lines 128 may be oriented in a generally vertical direction and may increase the modulus along a vertical axis. An increased modulus along the vertical axis corresponds to the generally vertical orientation of the calf muscles. In exemplary aspects, the compression force and/or modulus of elasticity may be increased by the lines 128 by, for example, 1%, 2%, 5%, 10%, 15%, 20% up to 25%, or up to 50% or any value in between.

The spacing between the lines 128 may be configured to further modify the modulus of elasticity and/or compression force of the underlying area. With reference to FIG. 2, the lines 128 located closer to the lateral margin of the tight 100 may be spaced further apart (e.g., more offset area) than the lines 128 located closer to the medial margin of the tight 100. In exemplary aspects, the modulus of elasticity and/or compression force may be increased along the spacing gradient by, for example, 1%, 2%, 5%, 10%, 15%, 20% up to 25%, or any value in between with the greater increases associated with the greater spacing. The location and spacing associated with the lines 128 on the back portion of the tight 100 are exemplary only, and it is contemplated that other locations and other spacing gradients may be utilized in association with the tight 100.

The third zone 120 may comprise a small extension of the shapes 130 that are located on the front-facing or anterior side of the tights 100. The shapes 130 may occupy an area towards the lateral margin of the tight 100 at the upper portion of the third zone 120. The remainder of the back-facing side of the third zone 120 may comprise an extension of the lines 128 of the second zone 118 (now labelled as lines 132). Spacing between the lines 132 may be along a gradient with increased spacing in areas located near the lateral margin of the tight and decreased spacing in areas located near the medial margin of the tight 100. By locating the lines 132 on the back-facing or posterior side of the tight 100, orienting the lines 132 in a generally vertical direction, and by creating the spacing gradient as described, a beneficial level of compression may be provided over the vertically-oriented calf muscles. The location and spacing associated with the lines 132 on the back portion of the tight 100 are exemplary only, and it is contemplated that other locations and other spacing gradients may be utilized in association with the tight 100.

When the tight 100 is configured as a short, capri, a three-quarter tight, or as a half-tight, the positioning of the zones 116, 118 and 120 and their associated structure patterns generally remains the same. One difference, however, is that the second and/or third zones may be truncated resulting in a decreased length of these zones and a corresponding loss of some of the structure patterns. For example, the ribs 132 may be truncated or even eliminated when forming the capri, the three-quarter tight, or half-tight.

Figure 3:
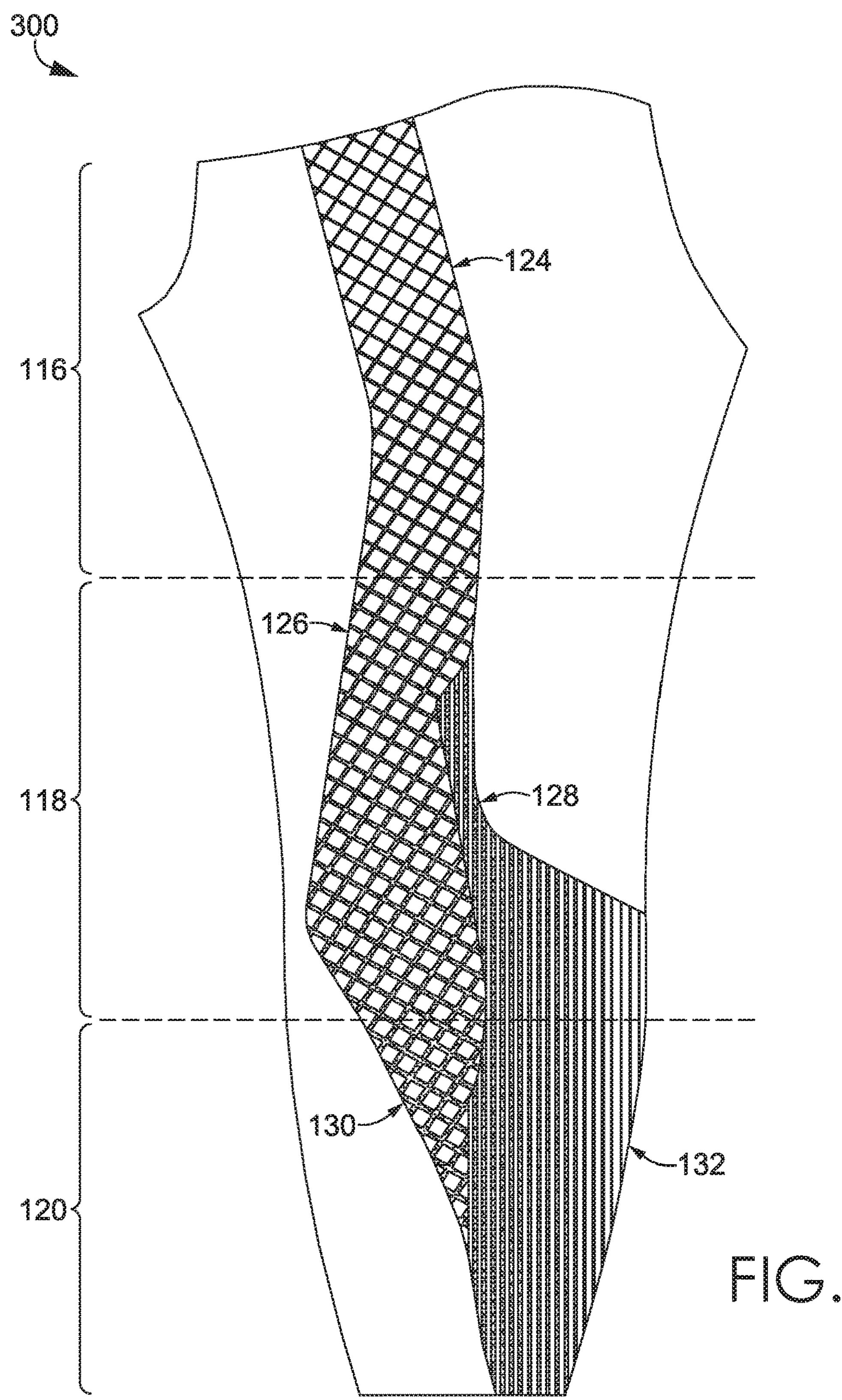
FIG. 3 illustrates a pattern piece used to construct an exemplary recovery tight with preconfigured compression zones and integrated structure patterns in accordance with an aspect herein.

Turning now to FIG. 3, a pattern piece 300 is depicted, where the pattern piece 300 may be cut from a panel of fabric knitted using, for instance, a single bar Jacquard warp knitting process. The panel of fabric may be knit to have the three linearly oriented compression zones discussed above and the integrated structure patterns. The pattern piece 300 may be used in part to form the recovery tight 100. For instance, the pattern piece 300 may correspond to a pattern piece for a left leg portion and may be joined to a pattern piece for a right leg portion at one or more seams to form the tight 100. The pattern piece 300, moreover, may cut to a number of different sizes so as to form different sizes of tights 100 and may be shaped differently to form tights for women versus men. Although the pattern piece 300 is shown with a length corresponding to a full tight, it is contemplated that the length may be shortened to form a capri, a half-tight, a three-quarter tight, or a short. The compression zones 116, 118 and 120 are depicted along with the structures 124, 126, 128, 130 and 132 as shown and described in relation to FIGS. 1 and 2. Moreover, the spacing between the structures that was described above with respect to FIGS. 1 and 2 is better shown in FIG. 3.

Figure 9:
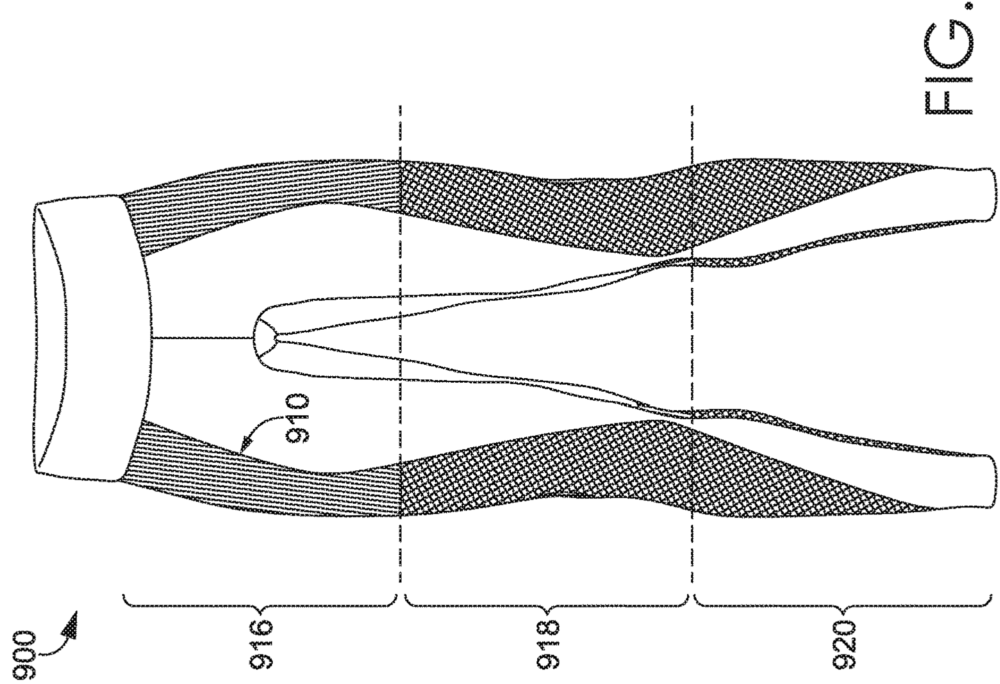
FIG. 9 illustrates a front view of an exemplary recovery tight with preconfigured compression zones and integrated structure patterns in accordance with an aspect herein.

FIG. 9 depicts a front view of another exemplary recovery tight 900 having horizontally-oriented compression zones and integrated knit structure patterns in accordance with an aspect herein. The compression zones 916, 918, and 920 generally correspond to the compression zones 116, 118, and 120 of the recovery tight 100. As such, the compression force associated with these different zones may be the same as the compression force associated with the compression zones 116, 118, and 120 of the tight 100.

The recovery tight 900 illustrates an alternative integrated knit structure pattern comprising a series of vertically-oriented lines 910 located along the lateral margin of the tight 900 in the first compression zone 916. The vertical orientation of the lines 910 may cause the modulus in the underlying area to be increased along a vertical axis. An increased modulus along the vertical axis may correspond to the generally vertical orientation of the thigh muscles. In exemplary aspects, the compression force and/or modulus of elasticity may be increased by the lines 910 by, for example, 1%, 2%, 5%, 10%, 15%, 20%, up to 25%, up to 50%, or any value in between. In exemplary aspects, the lines 910 may be spaced apart by a spacing gradient as described herein. The location and spacing associated with the lines 910 on the front portion of the tight 900 are exemplary only, and it is contemplated that other locations and other spacing gradients may be utilized in association with the tight 900.

The integrated knit structure patterns of the second zone 918 and the third zone 920 along the front portion of the tight 900 are generally the same as the integrated knit structure patterns of the second compression zone 118 and third compression zone 120 of the tight 100 and, as such, the discussion regarding those structure patterns is equally applicable here.

Figure 10:
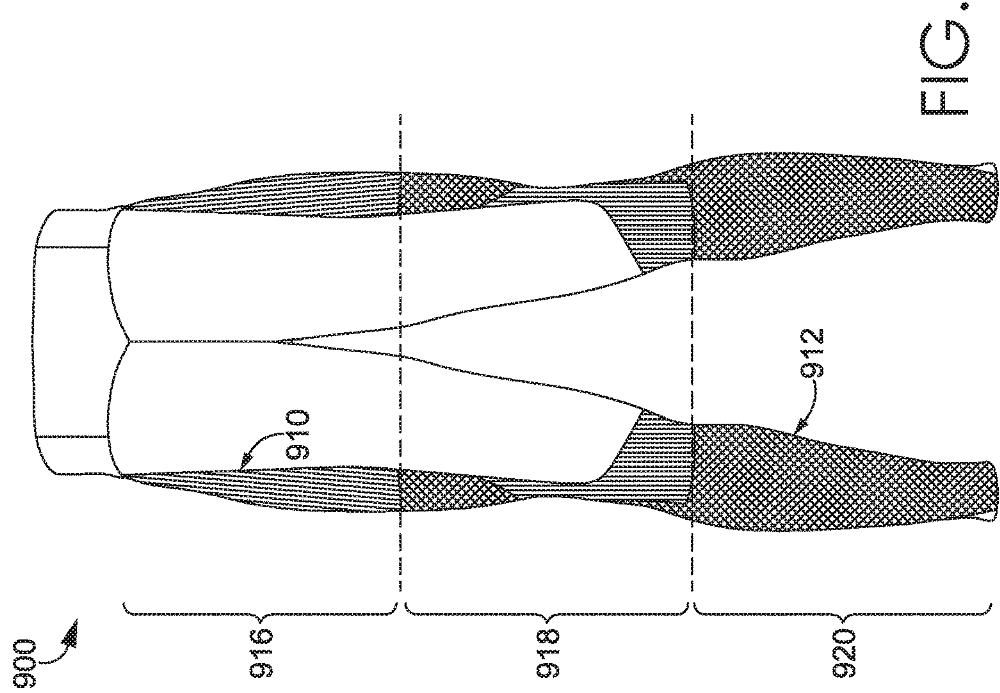
FIG. 10 illustrates a back view of the exemplary recovery tight with preconfigured compression zones and integrated structure patterns of FIG. 9 in accordance with an aspect herein.

Turning now to FIG. 10, a back view of the recovery tight 900 is depicted in accordance with an aspect herein. In exemplary aspects, the first zone 916 on the back of the tight 900 comprises the lines 910 as they extend around the lateral margin of the tight 900. The location and spacing associated with the lines 910 on the back portion of the tight 900 are exemplary only, and it is contemplated that other locations and other spacing gradients may be utilized in association with the tight 900. The integrated knit structure pattern of the second zone 918 on the back portion of the tight 900 is generally the same as the integrated knit structure pattern of the second compression zone 118 of the tight 100 and, as such, the discussion regarding that structure pattern is equally applicable here.

In exemplary aspects, the third compression zone 920 on the back side of the tight may comprise a series of shapes 912 that occupy the entirety of the back side of the third compression zone 920 and provide an added level of compression to the calf area of the wearer. Spacing between the shapes 912 may be along a gradient as described herein. The location and spacing associated with the shapes 912 on the back portion of the tight 900 are exemplary only, and it is contemplated that other locations and other spacing gradients may be utilized in association with the tight 900.

Although the zones associated with the recovery tights 100 and the recovery tights 900 are generally shown as comprising horizontally oriented bands formed through a single bar Jacquard warp knitting process, it is contemplated herein that the compression zones may comprise organically shaped (e.g., curvilinear) areas. As used in this disclosure, the term "organically shaped" generally means a shape having one or more curved or non-linear segments. For example, when textile panels used to form the exemplary recovery tight described herein are knit using a double bar Jacquard warp knitting process, one bar may be used to carry the elastic yarns that are used to impart the compression characteristics of the tight, while the other bar may be used to carry other yarns (e.g., polyester yarns) used to form the tights. The bar carrying the elastic yarns may be used to drop in stitches were needed to create more organically shaped compression zones.

Figure 12:
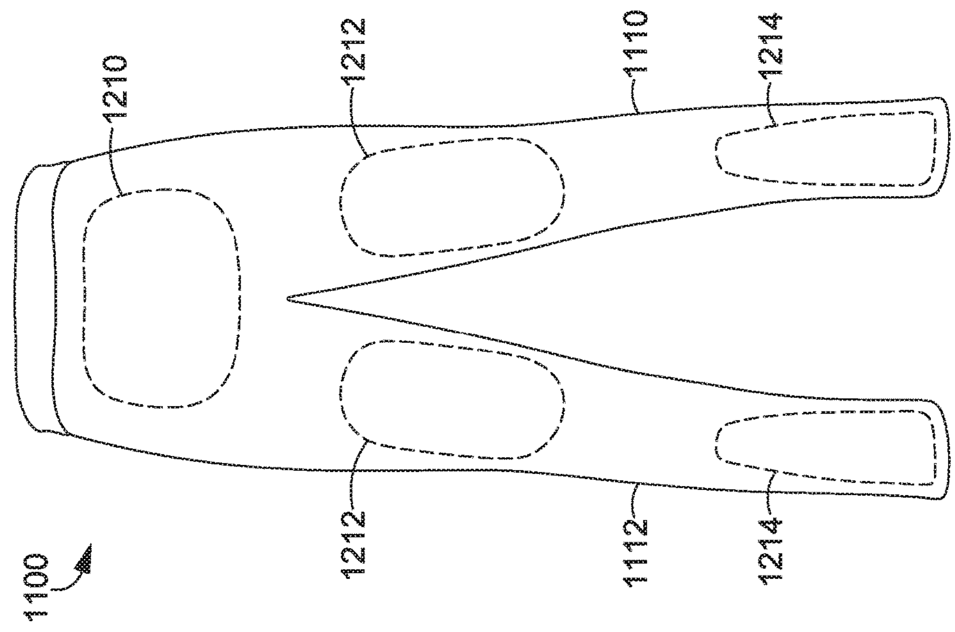
FIG. 12 illustrates a back view of the exemplary recovery tight of FIG. 11 in accordance with aspects herein.
Figure 11:
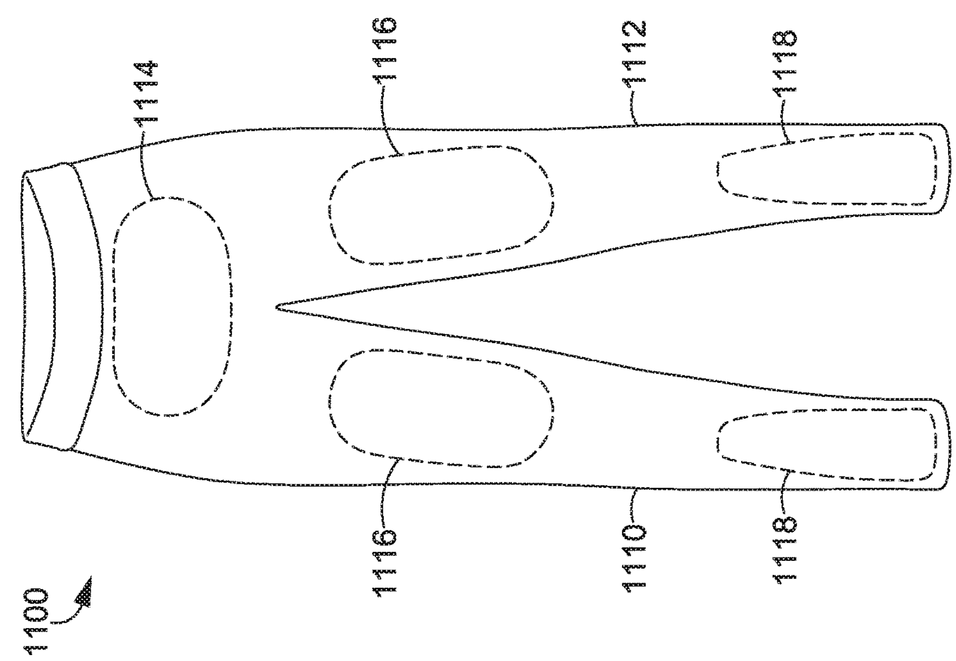
FIG. 11 illustrates a front view of an exemplary recovery tight with organically shaped compression zones in accordance with aspects herein.

An exemplary recovery tight incorporating organically shaped compression zones generated through, for instance, a double bar Jacquard warp knitting process is depicted in FIGS. 11 and 12 in accordance with aspects herein. FIG. 11 depicts a front view of an exemplary recovery tight 1100, and FIG. 12 depicts a back view of the exemplary recovery tight 1100. The recovery tight 1100 may have a torso portion, and at least a first leg portion 1110 and a second leg portion 1112. With respect to FIG. 11, a low modulus compression zone 1114 (shown by dashed lines) may be located at an anterior aspect of the torso portion such that it generally is positioned adjacent to a lower abdomen area of a wearer when the tight 1100 is worn. The compression force associated with the zone 1114 may be the same or similar to that recited for the first compression zone 116 of the tight 100. Providing a relatively low degree of compression in this area may help to impart some core stability to the wearer while still providing a relatively free range of motion.

Compression zones 1116 are shown as generally being located at an anterior aspect of the tight 1100 at a mid-portion of the first leg portion 1110 and the second leg portion 1112. When the recovery tight 1100 is worn, the compression zones 1116 would generally be positioned adjacent to a lower anterior thigh and an anterior knee area of the wearer. The compression force associated with the compression zones 1116 may be the same or similar to that recited for the second compression zone 118 of the tight 100. Because the elastic yarns are dropped in where needed, the compression zones 1116 may assume a more organic shape thereby allowing the compression zones 1116 to provide a medium level of compression to, for instance, the lower thigh and knee area of the wearer.

Compression zones 1118 are shown as generally being located at an anterior aspect of the lower portions of the first leg portion 1110 and the second leg portion 1112. When the recovery tight 1100 is worn, the compression zones 1118 would be generally positioned adjacent to a shin and ankle area of the wearer. The compression force associated with the compression zones 1118 may be the same or similar to that recited for the third compression zone 120 of the tight 100. Because the elastic yarns are dropped in where needed, the compression zones 1118 may assume a more organic shape thereby allowing the compression zones 1118 to provide a relatively high level of compression to, for instance, the shin and ankle area of the wearer thus helping any edema in this area to be "pushed" upward where it can more easily be resorbed.

FIG. 12, which depicts a back view of the tight 1100 further depicts compression zones 1210 located over a posterior aspect of the lower torso portion of the tight 1100. When worn, the compression zone 1210 would be positioned adjacent to a wearer's buttocks region. The compression force associated with the compression zone 1210 may be the same or similar to that recited for the first compression zone 116 of the tight 100. Because the elastic yarns are dropped in where needed, the compression zone 1210 may assume a more organic shape thereby allowing the compression zone 1210 to provide a targeted compression to, for instance, the posterior lower torso area of the wearer.

The tight 1100 may further comprise compression zones 1212 positioned at a mid-portion of the first leg portion 1110 and the second leg portion 1112. When the recovery tight 1100 is worn, the compression zones 1212 would generally be positioned generally adjacent to a lower posterior thigh and posterior knee area of the wearer. The compression force associated with the compression zones 1212 may be the same or similar to that recited for the second zone 118 of the tight 100. Because the elastic yarns are dropped in where needed, the compression zones 1212 may assume a more organic shape thereby allowing the compression zones 1212 to provide a moderate level of compression to, for instance, the poster thigh and posterior knee area of the wearer.

Compression zones 1214 may be positioned over a lower posterior portion of the first leg portion 1110 and the second leg portion 1112. When worn, the compression zones 1214 would be positioned adjacent to the calf muscles and ankle area of the wearer. The compression force associated with the compression zones 1214 may be the same or similar to that recited for the third compression zone 120 of the tight 100. Because the elastic yarns are dropped in where needed, the compression zones 1214 may assume a more organic shape thereby allowing the compression zones 1214 to provide a high level of targeted compression to, for instance, the calf muscles and ankle area of the wearer. Additional organically shaped compression zones are contemplated herein.

Although not shown, it is contemplated herein that integrated knit structure patterns may be associated with the compression zones 1114, 1116, 1118, 1210, 1212, and 1214 of the tight 1100 to modify the compression force of the compression zones as desired. It is further contemplated herein that the shape configuration for the compression zones may differ from that shown in FIGS. 11 and 12. Moreover, it is contemplated herein that the tight 1100 may comprise additional compression zones than those shown (i.e., compression zones located over the lateral sides of the tight 1100), or may comprise fewer compression zones than those shown. Any and all aspects, and any variation thereof, are contemplated as being within aspects herein.

Figure 6:
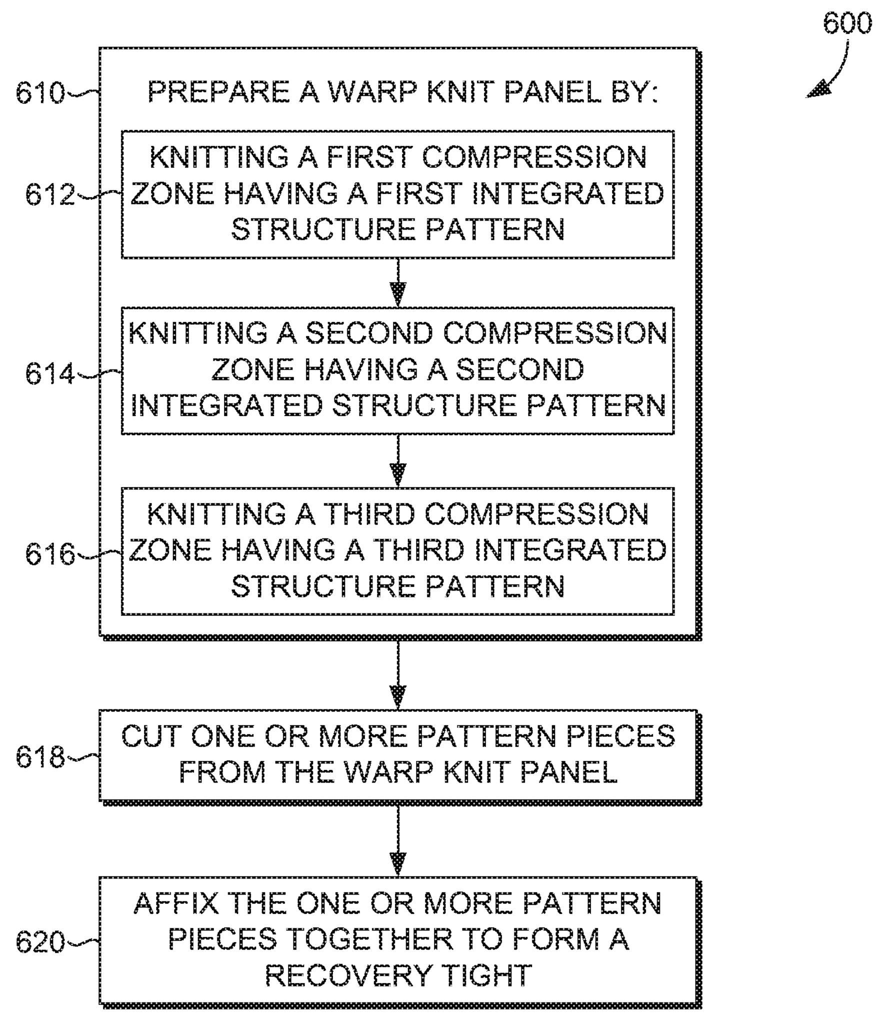
FIG. 6 illustrates a flow diagram of an exemplary method of manufacturing a warp knit recovery tight having preconfigured compression zones and integrated knit structure patterns in accordance with an aspect herein.

FIG. 6 illustrates a flow diagram of an exemplary method 600 of manufacturing a warp knit recovery tight such as the recovery tight 100, the recovery tight 900, or the recovery tight 1100. At a step 610, a fabric panel is prepared. The fabric panel may be prepared by utilizing a warp knitting process (single or double bar Jacquard) to knit a first compression zone, such as the first compression zone 116 or the compression zones 1114/1210, having a first modulus of elasticity and/or compression force at a step 612. The first compression zone may be formed using one or more elastic yarns having the same or different denier and having a predefined modulus of elasticity. The modulus of elasticity associated with the elastic yarn(s) may be due to the denier and/or diameter of the yarn, and/or due to the type of yarn used. Knitting the first compression zone may further comprise knitting a first integrated knit structure pattern as described herein.

At a step 614, a second compression zone, such as the second compression zone 118 or the compression zones 1116/1212, is knitted where the second compression zone is adjacent to the first compression zone. The second compression zone has a second modulus of elasticity and/or compression force that is greater than the first modulus of elasticity and/or compression force associated with the first compression zone. The second compression zone may be formed using one or more elastic yarns having the same or different denier. The modulus of elasticity of the yarns used to knit the second compression zone is greater than the modulus of elasticity of the yarns used to knit the first compression zone. Knitting the second compression zone may comprise knitting a second integrated knit structure pattern as described herein.

At a step 616, a third compression zone, such as the third compression zone 120 or the compression zones 1118/1214, is knitted where the third compression zone is adjacent to the second compression zone. The third compression zone has a third modulus of elasticity and/or compression force that is greater than the first modulus of elasticity and/or compression force associated with the first compression zone and the second modulus of elasticity and/or compression force associated with the second compression zone. The third compression zone may be formed using elastic yarns having a modulus of elasticity greater than the modulus of elasticity of the yarns used to knit the first compression zone and the second compression zone. Knitting the third compression zone may comprise knitting a third integrated structure pattern as described herein.

Continuing with the method 600, at a step 618, one or more pattern pieces may be cut from the warp knit fabric panel. And at a step 620, the one or more pattern pieces may be affixed together to form the recovery tight. The pattern pieces may differ when forming a tight for a man versus for a woman, when forming tights of different sizes, and/or when forming the tight as a capri, a half-tight, a three-quarter tight, and the like.

When knitting the panel using, for instance, a single bar Jaquard warp knitting process, the transition between the different compression zones may be configured in a gradient fashion or as more of an abrupt transition. For instance, an abrupt transition between the different compression zones may occur by setting up the warp such that yarns associated with, for instance, a first compression zone may be replaced with the yarns that will be used to form a second compression zone at the junction or demarcation between the two zones.

Figure 7:
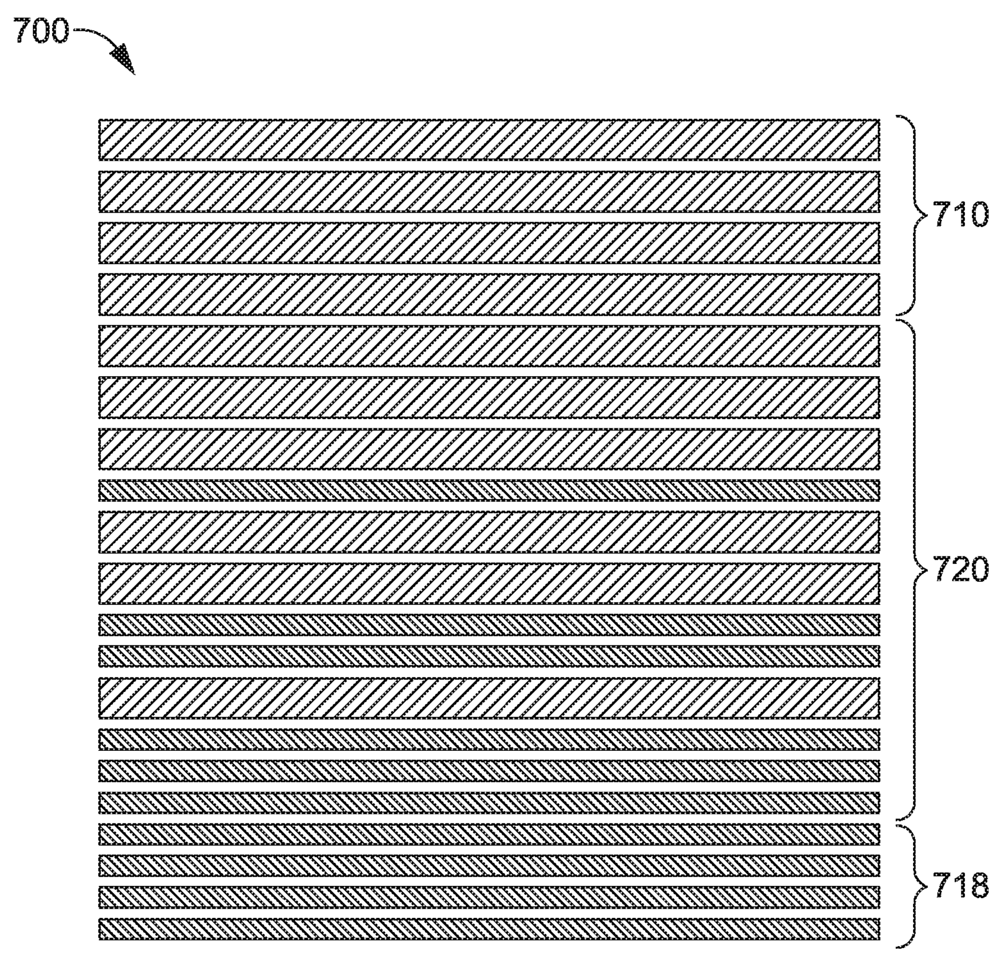
FIG. 7 illustrates a close-up view of an exemplary transition zone between a first compression zone and a second compression zone in accordance with an aspect herein.

In another exemplary aspect, the transition between the different compression zones may occur gradually by setting up the warp such that yarns used to knit a first compression zone are intermixed with yarns used to form a second compression zone at a transition area. An exemplary transition between different compression zones is shown in FIG. 7 and is referenced generally by the numeral 700. Reference numeral 710 indicates a first segment of warp yarns used to form a particular compression zone, such as, for example, the third compression zone 120. The yarns in the segment 710 may have a large denier or diameter and a high modulus. Segment 718 indicates a second segment of warp yarns used to form, for example, the second compression zone 118. The yarns in the segment 718 may have a smaller denier or diameter than the yarns in the segment 710 and a smaller modulus of elasticity. The segment 720 represents the transition area between the third compression zone and the second compression zone. As shown, the yarns of the first segment 710 are intermixed with the yarns of the second segment 718 in the transition segment 720. The pattern of the yarns in the transition segment 720 may vary. For instance, the intermixing of the yarns having the differing deniers may occur in a gradient fashion with the yarns associated with the first segment 710 gradually being replaced with the yarns associated with the second segment 718 so that the concentration of yarns having the larger denier is greater adjacent to the third compression zone and the concentration of yarns having the smaller denier is greater adjacent to the second compression zone. This is just one exemplary pattern and other transition patterns are contemplated herein. Because the transition segment 720 comprises an intermixing of the yarns having the differing deniers and differing moduli of elasticity, the modulus of elasticity of the transition segment 720 may be between the modulus of elasticity of the first segment 710 and the second segment 718.

As described above, the panel may also be knit using a double bar Jacquard warp knitting process that allows the elastic yarns to be dropped in where needed. As such, there may not be a transition area such as that described with respect to FIG. 7 between the different compression areas or zones.

In exemplary aspects, the recovery tight described herein may have color variation effect that is achieved by one of several methods. In one exemplary aspect, the color variation effect may comprise a dark colored tight with lighter-colored offset areas. This may be achieved by using, for instance, a cationic polyester yarn as the face yarn and, for example, a regular polyester yarn as the back yarn. In this aspect, the elastic yarns are uncolored. During the dyeing process, which may occur prior to the yarns being knitted to form the tight, the cationic polyester yarn may be dyed a dark color and the regular polyester yarn may be dyed a lighter color. By utilizing this stitch configuration and this dyeing process, the offset areas will be lighter in color than the remaining portions of the tight.

In another exemplary aspect, the color variation may comprise an iridescent effect in the solid-colored areas. This may be achieved by using a cationic polyester yarn as the face yarn and a regular polyester yarn as the back yarn. Again, the elastic yarns are uncolored. Similar to above, the cationic polyester yarn may be dyed a dark color and the regular polyester yarn may be dyed a lighter color. However, during the knitting of the tight, the stitch pattern is altered to allow a small amount of the lighter-colored back yarns to show through the dark-colored face yarns, thereby creating the iridescent effect. The offset areas, like above, are lighted colored.

In yet another exemplary aspect, the color variation may comprise a light colored tight with darker-colored offset areas. In this aspect, the regular polyester yarn comprises the face yarn and the cationic polyester yarn comprises the back yarn. During the dyeing process, the cationic polyester yarn may be dyed a dark color and the regular polyester yarn may be dyed a lighter color. By utilizing this dyeing process and this stitch configuration, the offset areas will be darker in color than the remaining portions of the tight.

Continuing, an additional type of iridescent effect may be achieved by using regular polyester yarn as the face yarn and a cationic polyester yarn as the back yarn. The cationic polyester yarn may be dyed a dark color and the regular polyester yarn may be dyed a lighter color. During the knitting of the tight, the stitch pattern is altered to allow a small amount of the darker-colored back yarn to show through light-colored face yarn, thereby creating the iridescent effect. The offset area are dark colored in this aspect.

In exemplary aspects, the elastic yarns may be covered with a polyester or cationic polyester yarn during spinning. The covered elastic yarn may then be dyed and incorporated into the tight in a manner similar to those described above to create the color variation effects noted above. Any and all such aspects, and any variation thereof, are contemplated as being within the scope herein.

Figure 8:
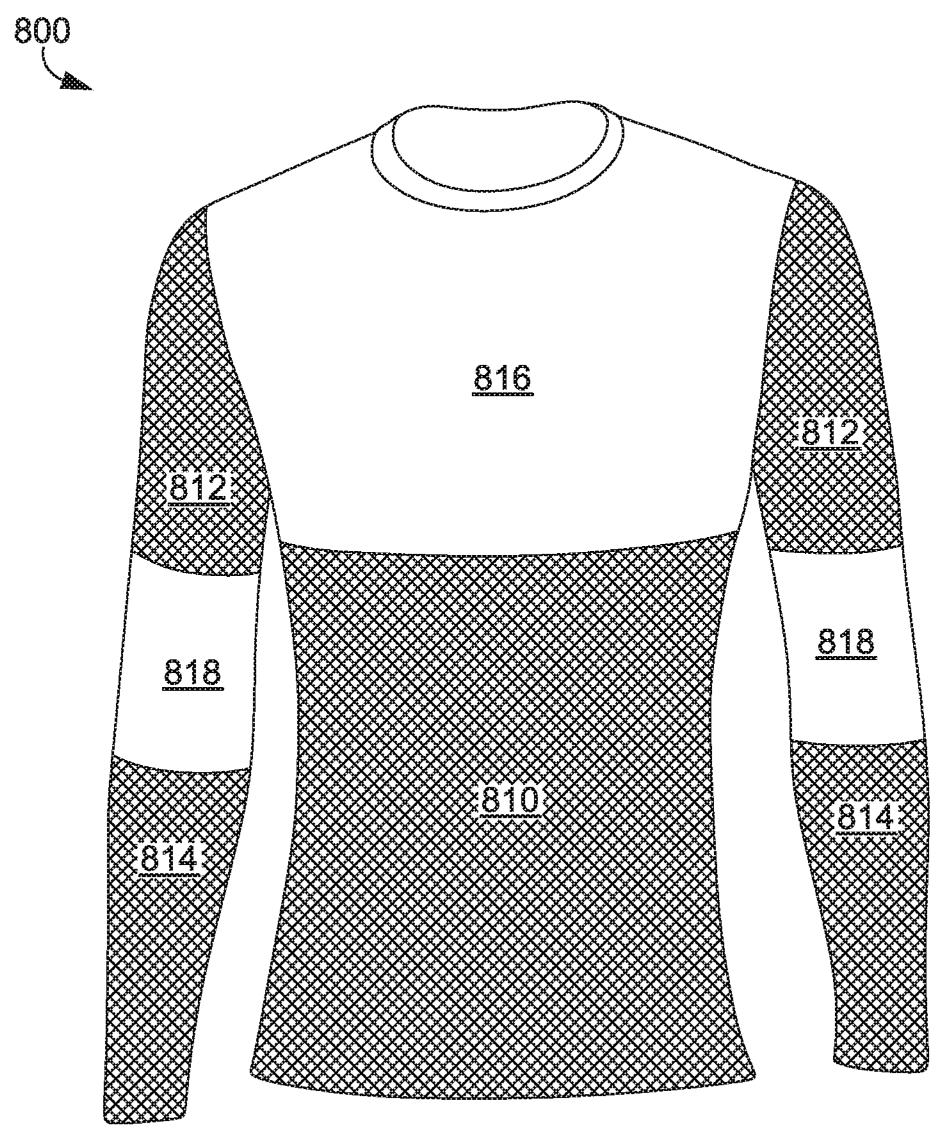
FIG. 8 illustrates an exemplary article of apparel for an upper torso of a wearer, the article of apparel having preconfigured compression zones in accordance with an aspect herein.

FIG. 8 illustrates an exemplary article of apparel 800 for an upper torso of a wearer in accordance with an aspect herein. The article of apparel 800 is in the form of a long-sleeve shirt although other articles are contemplated herein such as a sleeveless tank top, a camisole, a bra, a short-sleeved shirt, and the like. The article of apparel 800 may be formed from a warp knitted fabric (single or double bar Jaquard), where the fabric is knitted to have different compression zones and/or different integrated knit structure patterns as described herein. In the exemplary aspect shown in FIG. 8, the article of apparel 800 is configured to have high compression zones over the wearer's torso area 810, upper arm area 812, and lower arm area 814, and low to medium compression zones over the wearer's upper chest area 816, and elbow area 818. This configuration may, for instance, further help to stabilize the wearer's core, and minimize muscle vibration in the wearer's biceps and triceps while still providing mobility over the wearer's shoulder area and elbow area.

The configuration shown in FIG. 8 is exemplary only and it is contemplated herein that additional compression zone configurations may be used to achieve different functional purposes. For example, a high compression zone may be located over the wearer's lower back to help stabilize this area. Moreover, the integrated knit structure pattern in the form of repeating diamonds shown in FIG. 8 is exemplary only and it is contemplated herein that the apparel item 800 may have different structure patterns such as those shown in FIGS. 5A-5*s* or may not have any integrated structure patterns. Further, these structure patterns may be in different locations than those shown in FIG. 8. Any and all such aspects, and any variation thereof, are contemplated as being within the scope herein. The structure patterns may be used to further customize the amount of compression or the direction of compression associated with one or more of the compression zones as discussed herein.

From the foregoing, it will be seen that aspects herein are well adapted to attain all the ends and objects hereinabove set forth together with other advantages which are obvious and which are inherent to the structure. It will be understood that certain features and subcombinations are of utility and may be employed without reference to other features and subcombinations. This is contemplated by and is within the scope of the claims. Since many possible aspects may be made without departing from the scope thereof, it is to be understood that all matter herein set forth or shown in the accompanying drawings is to be interpreted as illustrative and not in a limiting sense.

What is claimed is:

1. A recovery tight having a non-planar outer-facing surface and a planar inner-facing surface, the recovery tight comprising:
- a plurality of compression zones, wherein:
- each of the plurality of compression zones has a compression force within a predefined range, and
- one or more of the plurality of compression zones has an integrated structure pattern comprising a plurality of offset areas extending inwardly from the outer-facing surface of the recovery tight, the plurality of offset areas comprising a shorter length knit stitch, and wherein:
  - the plurality of offset areas delineate and define a plurality of structures,
  - the shorter length knit stitch used to form the plurality of offset areas comprises a short length compared to a length of a knit stitch used to form the plurality of structures, and
  - the plurality of offset areas within the integrated structure pattern has a higher compression force compared to remaining areas within the one or more of the plurality of compression zones without the integrated structure pattern.

2. The recovery tight of claim 1, wherein the recovery tight is warp knitted.

3. The recovery tight of claim 1, wherein the integrated structure pattern is located at preconfigured locations within the respective compression zone.

4. The recovery tight of claim 3, wherein adjacent structures of the plurality of structures are spaced apart from one another by the plurality of offset areas.

5. The recovery tight of claim 4, wherein an amount of spacing between the adjacent structures of the plurality of structures modifies the compression force at the preconfigured locations.

6. The recovery tight of claim 4, wherein an increase in spacing between the adjacent structures of the plurality of structures increases the compression force at the preconfigured locations a greater amount compared to a decrease in spacing between the adjacent structures of the plurality of structures.

7. A recovery tight having a non-planar outer-facing surface and a planar inner-facing surface, the recovery tight comprising:
- a plurality of compression zones comprising:
- a first compression zone having a first compression force within a predefined range, the first compression zone located at an upper portion of the recovery tight;
- a second compression zone having a second compression force within a predefined range, the second compression zone located adjacent to and below the first compression zone; and
- a third compression zone having a third compression force within a predefined range, the third compression zone located adjacent to and below the second compression zone, wherein one or more of the first compression zone, the second compression zone, and the third compression zone comprises an integrated structure pattern comprising a plurality of offset areas extending inwardly from the outer-facing surface of the recovery tight, the plurality of offset areas comprising a shorter length knit stitch, wherein the plurality of offset areas within the integrated structure pattern has a higher compression force compared to remaining areas within the respective compression zone without the integrated structure pattern.

8. The recovery tight of claim 7, wherein the first compression force is less than the second compression force and the third compression force.

9. The recovery tight of claim 8, wherein the second compression force is less than the third compression force.

10. The recovery tight of claim 7, wherein:
- the first compression zone is located over a lower torso area and an upper thigh area of a wearer when the recovery tight is in an as-worn configuration;
- the second compression zone is located over a lower thigh area and a knee area of the wearer when the recovery tight is in the as-worn configuration; and
- the third compression zone is located over a calf area of the wearer when the recovery tight is in the as-worn configuration.

11. The recovery tight of claim 7, wherein the integrated structure pattern comprises a first integrated structure pattern and a second integrated structure pattern different from the first integrated structure pattern.

12. A method of manufacturing a recovery tight comprising:
- preparing a fabric having a first surface and an opposite second surface, wherein preparing the fabric comprises:
- knitting a first compression zone having a first compression force and a first integrated structure pattern;
- knitting a second compression zone having a second compression force and a second integrated structure pattern; and
- knitting a third compression zone having a third compression force and a third integrated structure pattern, wherein the first integrated structure pattern, the second integrated structure pattern, and the third integrated structure pattern comprise a plurality of offset areas extending inwardly from the first surface of the fabric, the plurality of offset areas comprising a shorter length knit stitch, wherein the plurality of offset areas within the first integrated structure pattern, the second integrated structure pattern, and the third integrated structure pattern have a higher compression force compared to remaining areas within the respective compression zones without the integrated structure pattern;
- cutting one or more pattern pieces from the fabric; and
- affixing the one or more pattern pieces together at one or more seams to form the recovery tight such that the first surface of the fabric forms an outer-facing surface of the recovery tight and the second surface forms an inner-facing surface of the recovery tight, wherein the inner-facing surface of the recovery tight is planar.

13. The method of manufacture of claim 12, wherein the first compression force is less than the second compression force and the third compression force, and wherein the second compression force is less than the third compression force.

14. The method of manufacture of claim 12, wherein the fabric is knitted using a warp knitting process.

15. The method of manufacture of claim 12, wherein the first compression force, the second compression force, and the third compression force of the first compression zone, the second compression zone, and the third compression zone respectively are dependent upon at least one of a diameter of an elastic yarn used to knit the first compression zone, the second compression zone, and the third compression zone or the type of yarn used to knit the first compression zone, the second compression zone, and the third compression zone.

16. The method of manufacture of claim 12, wherein the first integrated structure pattern, the second integrated structure pattern, and the third integrated structure pattern are integrally knitted using the same yarns as used to knit the first compression zone, the second compression zone, and the third compression zone respectively.

* * * * *